United States Patent
Novosad et al.

(10) Patent No.: US 11,842,497 B2
(45) Date of Patent: *Dec. 12, 2023

(54) AUTOMATIC CONTOUR ADAPTATION USING NEURAL NETWORKS

(71) Applicant: Elekta Limited, Montreal (CA)

(72) Inventors: Philip P. Novosad, Montreal (CA); Silvain Beriault, Longueuil (CA)

(73) Assignee: Elekta Limited, Montreal (CA)

(*) Notice: Subject to any disclaimer, the term of this patent is extended or adjusted under 35 U.S.C. 154(b) by 333 days.

This patent is subject to a terminal disclaimer.

(21) Appl. No.: 17/248,925

(22) Filed: Feb. 12, 2021

(65) Prior Publication Data

US 2022/0180523 A1    Jun. 9, 2022

Related U.S. Application Data

(60) Provisional application No. 63/199,144, filed on Dec. 9, 2020.

(51) Int. Cl.
*G06T 7/149* (2017.01)
*G06T 7/00* (2017.01)
(Continued)

(52) U.S. Cl.
CPC ............ *G06T 7/149* (2017.01); *A61N 5/1038* (2013.01); *A61N 5/1039* (2013.01);
(Continued)

(58) Field of Classification Search
CPC . G06T 2207/20081; G06T 2207/20084; G06T 2207/30004; G06T 2207/10088; G06T 7/11
See application file for complete search history.

(56) References Cited

U.S. PATENT DOCUMENTS 11,544,854 B2 *   1/2023   Novosad ................... G06T 7/11
2018/0070905 A1   3/2018   El-baz et al.
(Continued)

FOREIGN PATENT DOCUMENTS

WO    2020028382    2/2020
WO    2022120487    6/2022

OTHER PUBLICATIONS

"U.S. Appl. No. 17/248,926, Notice of Allowance dated Sep. 6, 2022", 9 pgs.
(Continued)

*Primary Examiner* — Gandhi Thirugnanam
(74) *Attorney, Agent, or Firm* — Schwegman Lundberg & Woessner, P.A.

(57) ABSTRACT

Systems and methods are disclosed for performing automatic contour adaptation. The systems and methods receive first and second images depicting an anatomy of a subject and obtain a segmentation associated with the first image. The systems and methods apply a trained neural network to estimate the adapted segmentation corresponding to the anatomy depicted in the second image, the trained network consisting of two sub-networks: a registration sub-network, generating an initial segmentation estimate representing a deformation of the segmentation associated with the first image to fit the anatomy depicted in the second image, and a segmentation refinement sub-network, predicting a refined segmentation for the second image given the initial segmentation estimate.

33 Claims, 17 Drawing Sheets

(51) Int. Cl.
  *G06T 7/33* (2017.01)
  *A61N 5/10* (2006.01)
  *G06T 5/00* (2006.01)
  *G06T 7/11* (2017.01)

(52) U.S. Cl.
  CPC ......... *A61N 5/1048* (2013.01); *A61N 5/1067* (2013.01); *G06T 5/008* (2013.01); *G06T 7/0012* (2013.01); *G06T 7/0014* (2013.01); *G06T 7/11* (2017.01); *G06T 7/33* (2017.01); *A61N 2005/1074* (2013.01); *G06T 2207/20081* (2013.01); *G06T 2207/20084* (2013.01); *G06T 2207/20116* (2013.01); *G06T 2207/30096* (2013.01)

(56) References Cited

U.S. PATENT DOCUMENTS

| | | | |
|---|---|---|---|
| 2019/0378278 | A1 | 12/2019 | Bose et al. |
| 2020/0104695 | A1 | 4/2020 | Laaksonen et al. |
| 2020/0129780 | A1 | 4/2020 | Lachaine et al. |
| 2020/0372669 | A1 | 11/2020 | Lachner et al. |
| 2021/0038921 | A1 | 2/2021 | Nguyen et al. |
| 2021/0046331 | A1* | 2/2021 | Lachaine ............. A61N 5/1068 |
| 2021/0220670 | A1 | 7/2021 | Li et al. |
| 2021/0290096 | A1 | 9/2021 | Yang et al. |
| 2021/0383538 | A1* | 12/2021 | Deasy ................. A61B 6/5211 |
| 2022/0012891 | A1 | 1/2022 | Nikolov et al. |
| 2022/0176157 | A1* | 6/2022 | Novosad ............. A61N 5/1067 |
| 2022/0180523 | A1* | 6/2022 | Novosad ................. G06T 7/33 |
| 2022/0180524 | A1* | 6/2022 | Novosad ................. G06T 7/149 |
| 2022/0375140 | A1* | 11/2022 | Mason ................... G06N 20/00 |
| 2022/0398717 | A1* | 12/2022 | Hébert ................... G06F 18/23 |

OTHER PUBLICATIONS

Eppenhof, K. A. J., "Fast contour propagation for MR-guided prostate radiotherapy using convolutional neural networks", Med. Phys. 47 (3), (Mar. 2020), 12 pg.

Heinrich, Mattias P, "MIND: Modality Independent Neighbourhood Descriptor for Multi-Modal Deformable Registration", Preprint submitted to Medical Image Analysis, (Sep. 19, 2014), 16 pgs.

Leger, Jean, "Contour Propagation in CT Scans with Convolutional Neural Networks", In: Proceedings of ACIVS, in Lecture Notes in ComputerScience book series., (2018), 13 pgs.

Petersen, Jorgen, "Deformable image registration for contour propagation from CT to cone-beam CT scans in radiotherapy of prostate cancer", Acta Oncologica, 50, (6), (2011), pp. 918-925.

Zhang, Lian, "The impact of robustness of deformable image registration on contour propagation and dose accumulation for head and neck adaptive radiotherapy", Radiatio Oncology Physics, (2017), 10 pgs.

Zhu, Jun-Yan, "Unpaired Image-to-Image Translation using Cycle-Consistent Adversarial Networks", arXiv:1703.10593 [cs.CV], (Aug. 24, 2020), 18 pgs.

"International Application Serial No. PCT CA2021 051769, International Search Report dated Mar. 7, 2022", 4 pgs.

"International Application Serial No. PCT CA2021 051769, Written Opinion dated Mar. 7, 2022", 4 pgs.

* cited by examiner

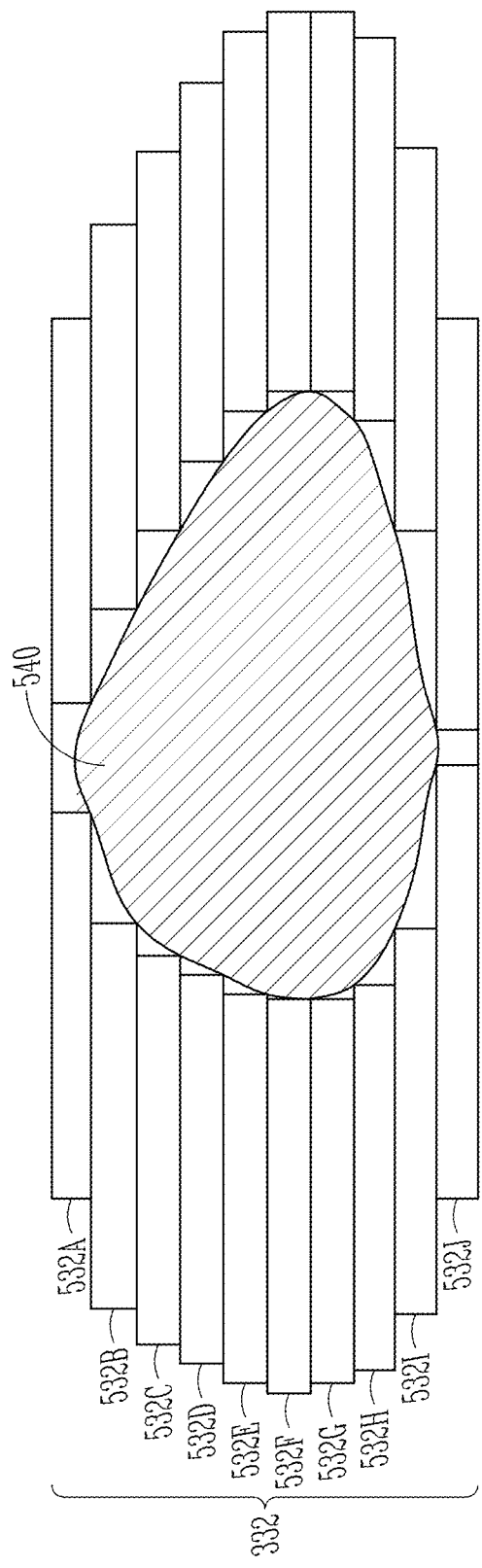

ность (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively, or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

AUTOMATIC CONTOUR ADAPTATION USING NEURAL NETWORKS

PRIORITY APPLICATIONS

This application claims the benefit of priority of U.S. Provisional Application Ser. No. 63/199,144, filed Dec. 9, 2020, which is hereby incorporated by reference in its entirety.

TECHNICAL FIELD

Embodiments of the present disclosure pertain generally to image segmentation in radiotherapy treatment.

BACKGROUND

Radiation therapy (or "radiotherapy") can be used to treat cancers or other ailments in mammalian (e.g., human and animal) tissue. One such radiotherapy technique involves irradiation with a Gamma Knife, whereby a patient is irradiated by a large number of low-intensity gamma ray beams that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various OARs because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, computed tomography (CT), nuclear magnetic resonance (MR), positron emission tomography (PET), single-photon emission computed tomography (SPECT), or ultrasound.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Since most patients receive more than one fraction of radiation as part of a course of therapy, and because the anatomy may change (deform) between these fractions, it is not straightforward to sum the doses delivered during the individual fractions so the physician can accurately gauge how the treatment is proceeding relative to the original intent as defined by the prescription.

OVERVIEW

In some aspects, a method is provided comprising: receiving first and second images depicting an anatomy of a subject, the first image corresponding to a previous radiotherapy treatment fraction, the second image corresponding to a current radiotherapy treatment fraction; obtaining a first image segmentation associated with the first image; applying a trained neural network to adapt the first image segmentation to the anatomy of the subject depicted in the second image, wherein applying the trained neural network comprises: applying a first sub-network of the trained neural network to the first image and the second image to generate an initial segmentation estimate representing a deformation of the first image segmentation to fit the anatomy depicted in the second image, the first sub-network being trained to establish a relationship between a plurality of previous treatment fraction images and subsequently obtained treatment fraction images; and applying a second sub-network to the initial segmentation estimate and the second image to predict a refined segmentation for the second image, the second sub-network being trained to establish a relationship between a plurality of initial segmentation estimates of a plurality of current fraction images and ground truth segmentations of the plurality of current fraction images; and configuring a radiotherapy treatment parameter based on the refined segmentation of the second image.

In some aspects, the first and second sub-networks are components of a single deep convolutional neural network for contour adaptation.

In some aspects, applying the first sub-network to the first image and the second image comprises: concatenating the first and second images along a channel dimension to generate concatenated data; and generating, based on a passing the concatenated data through the first sub-network, a deformation vector field (DVF) that maps pixels or voxels from the first image to the second image.

In some aspects, the method includes resampling the first image with the first image segmentation based on the DVF to produce an image-segmentation pair that aligns the first image to the second image.

In some aspects, the method includes deforming the first image segmentation based on the DVF.

In some aspects, applying the second sub-network to the initial segmentation estimate and the second image to predict the refined segmentation for the second image comprises: applying the second sub-network to the deformed segmentation and the second image to generate the refined segmentation.

In some aspects, the method includes converting one or more contours associated with the first image to label maps or binary segmentations to generate the first image segmentation.

In some aspects, configuring the radiotherapy treatment parameter comprises converting the refined segmentation of the second image to one or more contours associated with the second image.

In some aspects, the method includes determining a first modality of the first image; and adjusting a second image obtained using a second modality to correspond to the first modality of the first image.

In some aspects, configuring the radiotherapy treatment parameter comprises at least one of recalculating dose, adjusting one or more radiotherapy treatment machine parameters, or generating a display of the second image with the refined segmentation of the second image on a graphical user interface.

In some aspects, the method includes training the first and second sub-networks simultaneously by: obtaining a pair of training images and corresponding ground truth segmentations representing two treatment fractions; applying the first sub-network to the pair of training images and the ground truth segmentation corresponding to a first training image of the pair of training images to generate a first initial estimated segmentation; applying the second sub-network to a second training image of the pair of training images and the first initial estimated segmentation to generate a refined segmentation; computing a set of cost functions the set of cost functions including a term which measures a discrepancy between the refined segmentation and the ground truth segmentation; and adjusting one or more parameters of at least one of the first sub-network or the second sub-network based on the computed cost function.

In some aspects, computing the set of cost functions further comprises computing a cost function that includes a difference between a deformation of a given one of the plurality of previous treatment fraction images and a given one of the subsequently obtained treatment fraction images.

In some aspects, computing the set of cost functions further comprises computing an additional cost function that includes a difference between a deformation of a segmentation associated with a given one of the plurality of previous treatment fraction images and a ground truth segmentation of the given one of the subsequently obtained treatment fraction images.

In some aspects, computing the set of cost functions further comprises computing an additional cost function that includes a measure of smoothness of a generated deformation field.

In some aspects, the method includes training the first and second sub-networks in sequence by first adjusting one or more parameters of the first sub-network to minimize a first set of cost functions and then adjusting one or more parameters of the second sub-network to minimize a second set of cost functions.

In some aspects, the method includes training the first sub-network by: obtaining a pair of training images and corresponding ground truth segmentations representing two treatment fractions; applying the first sub-network to the pair of training images and the ground truth segmentation corresponding to a first training image in the pair of training images to generate at least one of a deformation of the first training image or a deformation of a segmentation of the first training image; computing a first set of cost functions, the set of cost functions including a term which measures a discrepancy between the initial segmentation and the ground truth segmentation corresponding to the second training image; and adjusting one or more parameters of the first sub-network based on the computed first set of cost functions.

In some aspects, the method includes training the second sub-network by: applying the second sub-network to the second training image and the first initial estimated segmentation to generate a refined segmentation; computing a second set of cost functions, the set of cost functions including a term which measures a discrepancy between the refined segmentation and the ground truth segmentation corresponding to the second training image; and adjusting one or more parameters of at least one of the first sub-network or the second sub-network based on the computed first or second sets of cost functions.

In some aspects, a computing apparatus is provided that includes: a processor; and a memory storing instructions that, when executed by the processor, configure the apparatus to: receive first and second images depicting an anatomy of a subject, the first image corresponding to a previous radiotherapy treatment fraction, the second image corresponding to a current radiotherapy treatment fraction; obtain a first image segmentation associated with the first image; apply a trained neural network to adapt the first image segmentation to the anatomy of the subject depicted in the second image, wherein applying the trained neural network comprises: applying a first sub-network of the trained neural network to the first image and the second image to generate an initial segmentation estimate representing a deformation of the first image segmentation to fit the anatomy depicted in the second image, the first sub-network being trained to establish a relationship between a plurality of previous treatment fraction images and subsequently obtained treatment fraction images; and applying a second sub-network to the initial segmentation estimate and the second image to predict a refined segmentation for the second image, the second sub-network being trained to establish a relationship between a plurality of initial segmentation estimates of a plurality of current fraction images and ground truth segmentations of the plurality of current fraction images; and configuring a radiotherapy treatment parameter based on the refined segmentation of the second image.

In some aspects, the first and second sub-networks are components of a single deep convolutional neural network for contour adaptation.

In some aspects, applying the first sub-network to the first image and the second image comprises: concatenating the first and second images along a channel dimension to generate concatenated data; and generating, based on a passing the concatenated data through the first sub-network, a deformation vector field (DVF) that maps pixels or voxels from the first image to the second image.

In some aspects, the instructions further configure the apparatus to: resample the first image with the first image segmentation based on the DVF to produce an image-segmentation pair that aligns the first image to the second image.

In some aspects, the instructions further configure the apparatus to: deform the first image segmentation based on the DVF.

In some aspects, applying the second sub-network to the initial segmentation estimate and the second image to predict the refined segmentation for the second image comprises: applying the second sub-network to the deformed segmentation and the second image to generate the refined segmentation.

In some aspects, the instructions further configure the apparatus to: convert one or more contours associated with the first image to label maps or binary segmentations to generate the first image segmentation.

In some aspects, configuring the radiotherapy treatment parameter comprises converting the refined segmentation of the second image to one or more contours associated with the second image.

In some aspects, the instructions further configure the apparatus to: determine a first modality of the first image; and adjust a second image obtained using a second modality to correspond to the first modality of the first image.

In some aspects, configuring the radiotherapy treatment parameter comprises at least one of recalculating dose, adjusting one or more radiotherapy treatment machine parameters, or generating a display of the second image with the refined segmentation of the second image on a graphical user interface.

In some aspects, the instructions further configure the apparatus to train the first and second sub-networks simultaneously by: obtaining a pair of training images and corresponding ground truth segmentations representing two treatment fractions; applying the first sub-network to the pair of training images and the ground truth segmentation corresponding to a first training image of the pair of training images to generate a first initial estimated segmentation; applying the second sub-network to a second training image of the pair of training images and the first initial estimated segmentation to generate a refined segmentation; computing a set of cost functions, the set of cost functions including a term which measures a discrepancy between the refined segmentation and the ground truth segmentation; and adjusting one or more parameters of at least one of the first sub-network or the second sub-network based on the computed cost function.

In some aspects, computing the set of cost functions further comprises computing an additional cost function that includes a difference between a deformation of a given one of the plurality of previous treatment fraction images and a given one of the subsequently obtained treatment fraction images.

In some aspects, computing the set of cost functions further comprises computing an additional cost function that includes a difference between a deformation of a segmentation associated with a given one of the plurality of previous treatment fraction images and a ground truth segmentation of the given one of the subsequently obtained treatment fraction images.

In some aspects, computing the set of cost functions further comprises computing an additional cost function that includes a measure of smoothness of a generated deformation field.

In some aspects, the instructions further configure the apparatus to train the first and second sub-networks in sequence by first adjusting one or more parameters of the first sub-network to minimize a first set of cost functions and then adjusting one or more parameters of the second sub-network to minimize a second set of cost functions.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIG. 5 illustrates an exemplary collimator configuration for shaping, directing, or modulating an intensity of a radiation therapy beam, according to some embodiments of the present disclosure.

DETAILED DESCRIPTION

Figure 1:
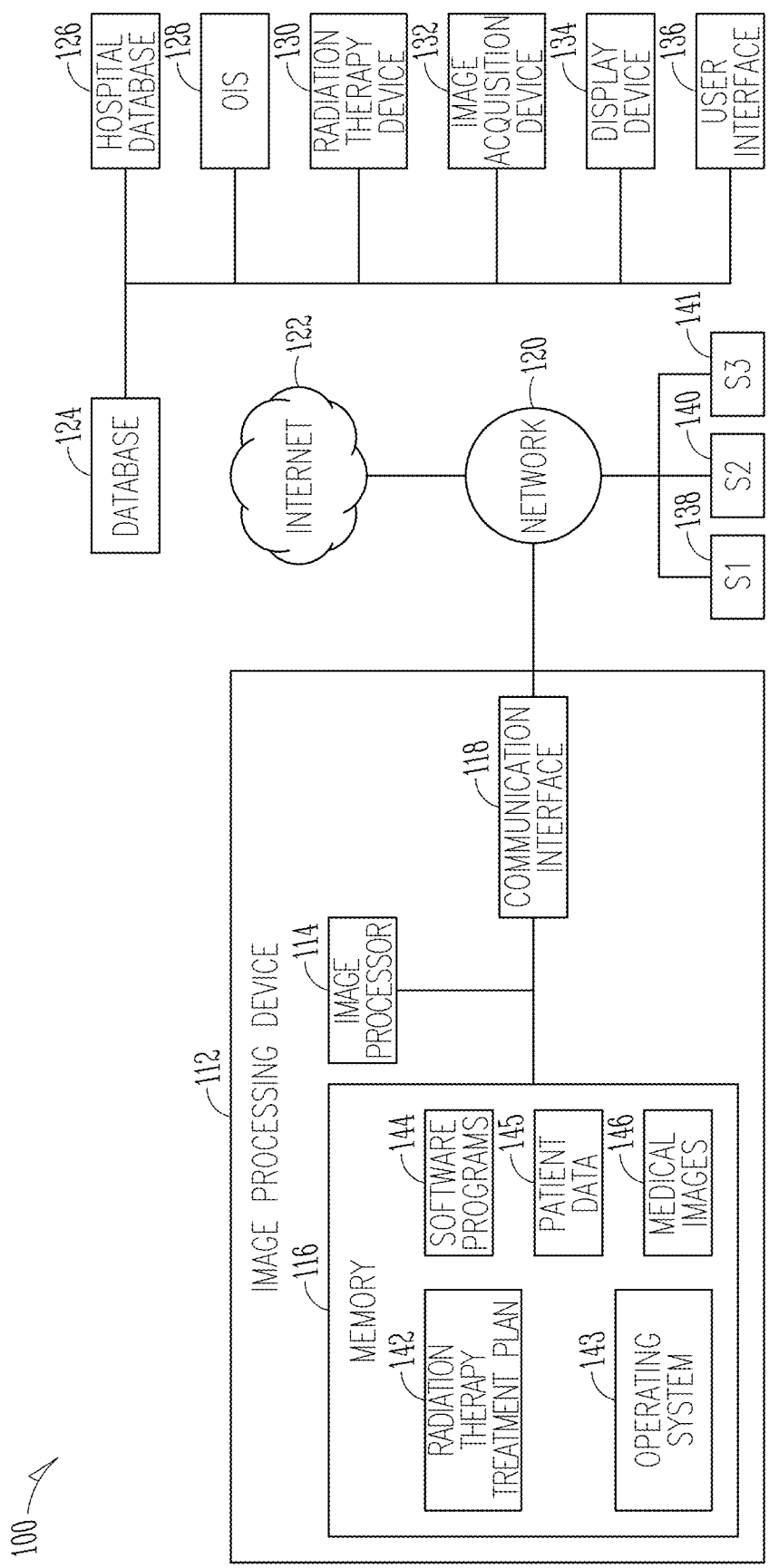
FIG. 1 illustrates an exemplary radiotherapy system, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not be taken in a limiting sense, and the scope of the present disclosure is defined by the appended claims and their equivalents.

An MR-Linac system combines a Linac with an on-board MR imaging system. This combined system allows for more precise treatment delivery by supporting (1) the acquisition of high-resolution 3D MR images with flexible contrast to guide treatment planning and to assess treatment response, and (2) real-time motion monitoring using continuously acquired two-dimensional (2D) MR images during treatment. With an MR-Linac, one can adapt and optimize radiotherapy treatment for each patient on a fraction-by-fraction basis by acquiring a daily MRI. Specifically, at each treatment fraction, the pre-treatment MRI (or CT), alongside the contours and treatment plan, are propagated to the daily MRI using one of two workflows: adapt-to-position (ATP) or adapt-to-shape (ATS).

In the ATP workflow, a translation between the pre-treatment image (CT or MRI) and the daily MRI is computed, and then the pre-treatment dataset and contours are shifted using the found translation. Dose recalculation and/or re-optimization is, in the ATP workflow, performed on the shifted pre-treatment dataset and contours, and the daily MRI is used only for re-positioning the pre-treatment dataset. Therefore, the ATP workflow, while simple and robust, does not account for fine-grained changes (e.g., organ deformation) that often occur between treatment fractions.

The ATS workflow allows for a more flexible and personalized plan adaptation based on the new patient anatomy as observed on the daily MR. In the first step, the pre-treatment dataset is deformably registered to the daily MRI, and the pre-treatment contours are propagated (e.g., deformed) onto the online planning MRI. Contours are then edited as necessary, and, together with the deformed pre-treatment dataset, a new plan is re-calculated and optimized.

Deformable image registration (DIR) is challenging, especially between modalities (e.g., CT-to-MR), and the results of inter-modality contour propagation in the ATS workflow are often sub-optimal. Indeed, clinicians spend an average of 11.5 minutes re-contouring the CT-to-MR propagated results in the ATS workflow. This inefficiency introduces a significant trade-off between treatment accuracy and treatment efficiency. To address this problem, certain systems provide various methods for automatic segmentation.

In one approach, independent segmentation models are applied directly on the daily MRI. In this approach, segmentation is performed independently on each daily MR image (e.g., using multi-atlas based segmentation or a convolutional neural network). Using deep convolutional neural networks, segmentation of many organs at risk has the potential to be highly accurate and efficient. This approach, though, does not leverage prior information (e.g., contours on previous fractions), which may result in sub-optimal performance, particularly for certain structures which often do not align well with visible anatomical boundaries (e.g., gross/cumulative target volumes). In addition, by ignoring prior contours from previous fractions, this approach cannot model differences in contouring style. Namely, this approach will always produce the same contours given the same image.

In another approach, deformable registration is used to propagate contours from previous fraction images (e.g., pre-treatment CT/MRI or the daily MRI from a previous fraction) to the current one. This approach may be more suitable for the segmentation of difficult target structures, and can also account for individual contouring styles. Namely, the propagated contour depends not only on the registration results but also on the style of the contour to be propagated. This approach may be a considerably slower option (particularly if using non-deep-learning deformation methods, which are the current standard in clinical practice), and deformable registration-based methods cannot recover contour errors due to imperfect registrations. Indeed, using deformable registration-based contour propagation alone may not produce sufficiently accurate contours, particularly when performing registration between modalities (e.g., CT-to-MR). Lastly, registration results are highly sensitive to the choice of registration algorithm and registration algorithm parameters.

According to some embodiments, a fully end-to-end deep learning approach is provided using convolutional neural networks for generating contours (segmentations) adapted to the anatomy exhibited on the daily MRI. Internally, the machine learning model (e.g., the convolutional neural network) includes a cascade of two sub-networks: the first sub-network performs registration-based segmentation propagation and produces a propagated segmentation; and the second sub-network refines the propagated segmentation.

In some cases, the first, second, and third sub-networks discussed above can be trained independently and separately from one another. In some cases, the first, second and third sub-networks are trained together in an end-to-end manner.

FIG. 1 illustrates an exemplary radiotherapy system 100 for providing radiation therapy to a patient. The radiotherapy system 100 includes an image processing device 112. The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, a processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114.

In one embodiment, the software programs 144 may convert medical images of one format (e.g., MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment the software programs 144 may substitute functions of the patient images or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In yet another embodiment, the software programs 144 may generate a refined segmentation for a current image received in a radiotherapy treatment fraction. For example, the software programs 144 may receive first and second images depicting an anatomy of a subject, with the first image corresponding to a previous radiotherapy treatment fraction and the second image corresponding to a current radiotherapy treatment fraction. The software programs 144 may obtain a first image segmentation associated with the first image and apply a trained neural network to adapt the first image segmentation to the anatomy of the subject depicted in the second image. Specifically, the software programs 144 may apply a first sub-network of the trained neural network to the first image and the second image to generate an initial segmentation estimate representing a deformation of the first image segmentation to fit the anatomy depicted in the second image, the first sub-network being trained to establish a relationship between a plurality of previous treatment fraction images and subsequently obtained treatment fraction images. The software programs 144 may apply a second sub-network to the initial segmentation estimate and the second image to estimate a refined segmentation for the second image, the second sub-network being trained to establish a relationship between a plurality of initial segmentation estimates of a plurality of current fraction images and ground truth segmentations of the plurality of current fraction images. A radiotherapy treatment parameter can then be configured based on the refined segmentation of the second image. For example, the radiotherapy treatment parameter can be reconfigured by recalculating dose, adjusting one or more radiotherapy treatment machine parameters, or generating a display of the second image with the refined segmentation of the second image on a graphical user interface.

In yet another embodiment, the software programs 144 may generate a refined segmentation for a current image received in a radiotherapy treatment fraction. For example, the software programs 144 may receive first and second images depicting an anatomy of a subject, the first image corresponding to a previous radiotherapy treatment fraction, the second image corresponding to a current radiotherapy treatment fraction. The software programs 144 may obtain a first image segmentation associated with the first image and apply a trained neural network to adapt the first image segmentation to the anatomy of the subject depicted in the second image. Specifically, the software programs 144 may apply a first sub-network of the trained neural network to the first image and the second image to generate a first initial segmentation estimate representing a deformation of the first image segmentation to fit the anatomy depicted in the second image, the first sub-network being trained to establish a relationship between a plurality of previous treatment fraction images and subsequently obtained treatment fraction images. The software programs 144 may apply a second sub-network to the second image to generate a second initial segmentation estimate for the second image, the second sub-network being trained to establish a relationship between a plurality of current treatment fraction images and corresponding ground truth segmentations. The software programs 144 may apply a third sub-network to the second image and the first and second initial segmentations to estimate a refined segmentation for the second image, the third sub-network being trained to establish a relationship between a plurality of pairs of initial segmentation estimates and the corresponding ground truth segmentations. A radiotherapy treatment parameter can then be configured based on the refined segmentation of the second image. For example, the radiotherapy treatment parameter can be reconfigured by recalculating dose, adjusting one or more radiotherapy treatment machine parameters, or generating a display of the second image with the refined segmentation of the second image on a graphical user interface.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may, include information such as (1) functional organ modeling data (e.g., serial versus parallel organs, appropriate dose response models, etc.); (2) radiation dosage data (e.g., DVH information); or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a machine learning model, such as a neural network model; or generate intermediate 2D or 3D images, which may then subsequently be stored in memory device 116. The processor 114 may subsequently transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software programs 144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory device 116, to perform various operations, processes, methods that will be explained in greater detail below.

The memory device 116 can store medical images 146. In some embodiments, the medical images 146 may include one or more MRI images (e.g., 2D MRI, 3D MRI, 2D streaming MRI, four-dimensional (4D) MRI, 4D volumetric MRI, 4D cine MRI, etc.), functional MRI images (e.g., fMRI. DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the image processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory device 116. The communication interface 118 may provide communication connections between the image processing device 112 and radiotherapy system 100 components (e.g., permitting the exchange of data with external devices). For instance, the communication interface 118 may, in some embodiments, have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI, pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories and optical and magnetic media. For example, the processor readable storage medium can be one or more volatile, non-transitory, or non-volatile tangible computer-readable media.

Image processor 114 may communicate with database 124 to read images into memory device 116 or store images from memory device 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, projection images, graphical aperture images, etc.) that the database 124 received from image acquisition device 132. Database 124 may store data to be used by the image processor 114 when executing software program 144 or when creating radiation therapy treatment plans 142. Database 124 may store the data produced by the trained machine learning mode, such as a neural network including the network parameters constituting the model learned by the network and the resulting estimated data. As referred to herein, estimate or estimated can be used interchangeably with predicted or predicted and should be understood to have the same meaning. The image processing device 112 may receive the imaging data, such as a medical image 146 (e.g., 2D MRI slice images, CT images, 2D Fluoroscopy images, X-ray images, 3D MRI images, 4D MRI images, projection images, graphical aperture images, image contours, etc.) from the database 124, the radiation therapy device 130 (e.g., an MR-linac), and/or the image acquisition device 132 to generate a treatment plan 142.

In an embodiment, the radiotherapy system 100 can include an image acquisition device 132 that can acquire medical images (e.g., MRI images, 3D MRI, 2D streaming MRI, 4D volumetric MRI, CT images, cone-Beam CT, PET images, functional MRI images (e.g., fMRI, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can be also stored by the image processing device 112, as medical image 146 in memory device 116.

In an embodiment, for example, the image acquisition device 132 may be integrated with the radiation therapy device 130 as a single apparatus (e.g., an MR-linac). Such an MR-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The image processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the image processor 114 may communicate with the image acquisition device 132 (e.g., a CT device, an MRI device, a PET device, an X-ray device, an ultrasound device, etc.) to access images of the patient and to delineate a target, such as a tumor, to generate contours of the images. In some embodiments, the delineation of one or more OARs, such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained and used to generate a contour of the image Contours of the image can include data overlaid on top of the image that delineates one or more structures of the anatomy. In some cases, the contours can be files associated with respective images that specify the coordinates or 2D or 3D locations of various structures of the anatomy depicted in the images.

In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may use to input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, and the image acquisition device 132 could be implemented as a virtual machine. Given the processing power, memory, and computational capability available, the entire radiotherapy system 100 could be implemented as a virtual machine.

Figure 2A:
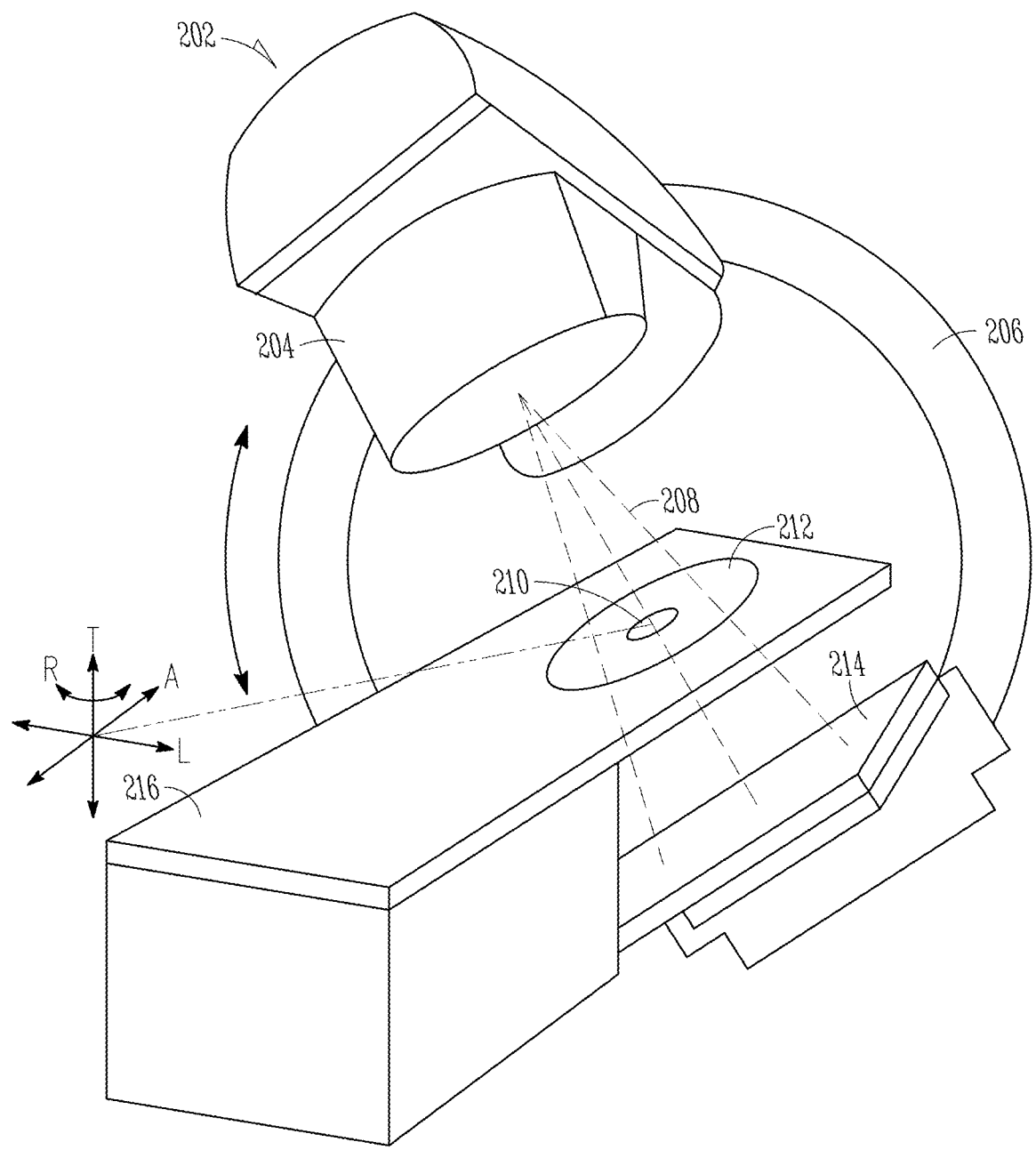
FIG. 2A illustrates an exemplary radiation therapy system that can include radiation therapy output configured to provide a therapy beam, according to some embodiments of the present disclosure.

FIG. 2A illustrates an exemplary radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC as described in the illustrative embodiment of FIG. 5, below.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch's 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can precisely target the tumor. The MLC may be integrated and included within gantry 206 to deliver the radiation beam 208 of a certain shape.

The coordinate system (including axes A, T, and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an embodiment, the imaging detector 214 can be located within a field of the therapy beam 208.

The imaging detector 214 can be mounted on the gantry 206 (preferably opposite the radiation therapy output 204), such as to maintain alignment with the therapy beam 208. The imaging detector 214 rotates about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided.

Figure 2B:
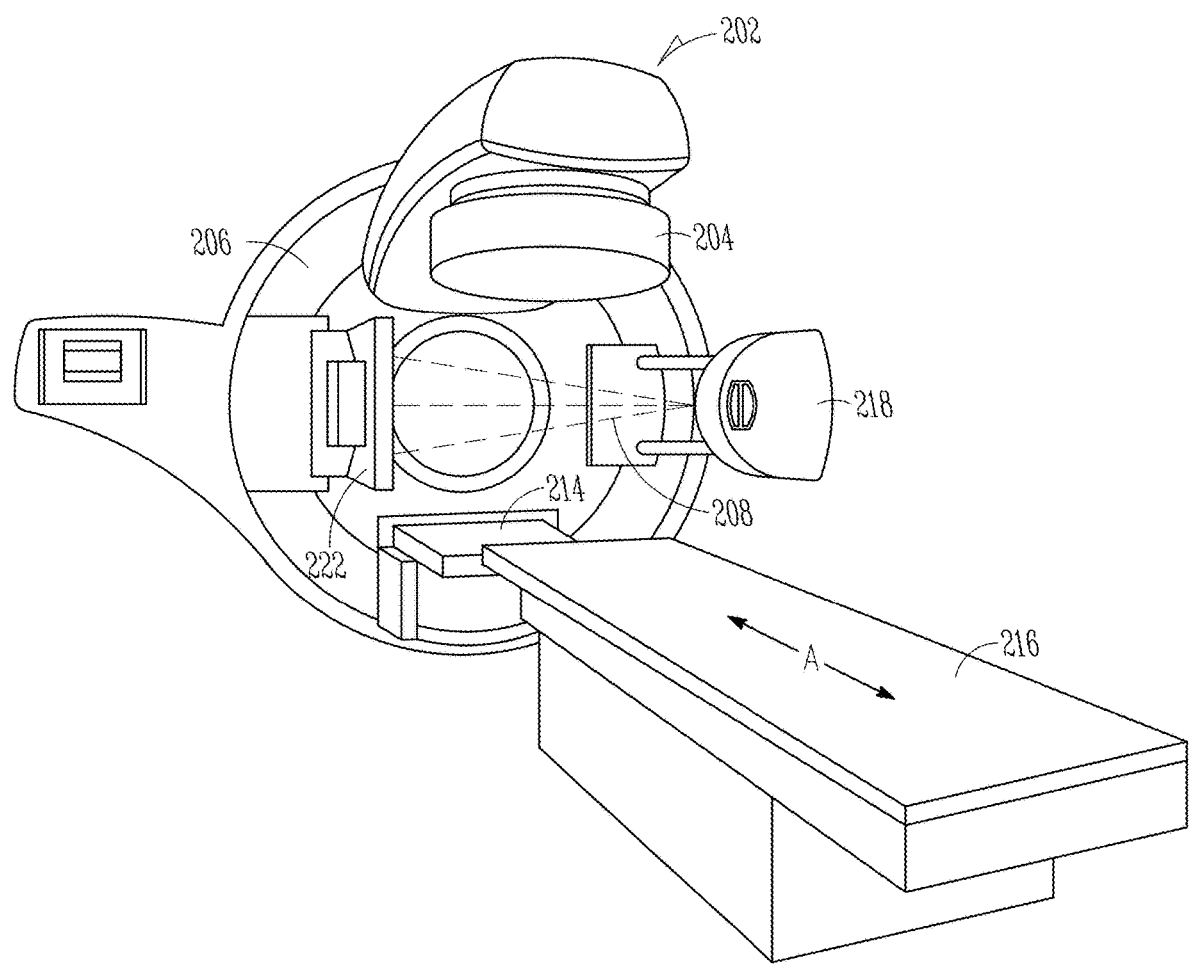
FIG. 2B illustrates an exemplary system including a combined radiation therapy system and an imaging system, such as a cone beam computed tomography (CBCT) imaging system, according to some embodiments of the present disclosure.

FIG. 2B illustrates an exemplary radiation therapy device 202 that may include a combined linac and an imaging system, such as can include a CT imaging system. The radiation therapy device 202 can include an MLC (not shown). The CT imaging system can include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

In the illustrative embodiment of FIG. 2B, the radiation therapy output 204 and the X-ray source 218 can be mounted on the same rotating gantry 206, rotationally-separated from each other by 90 degrees. In another embodiment, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
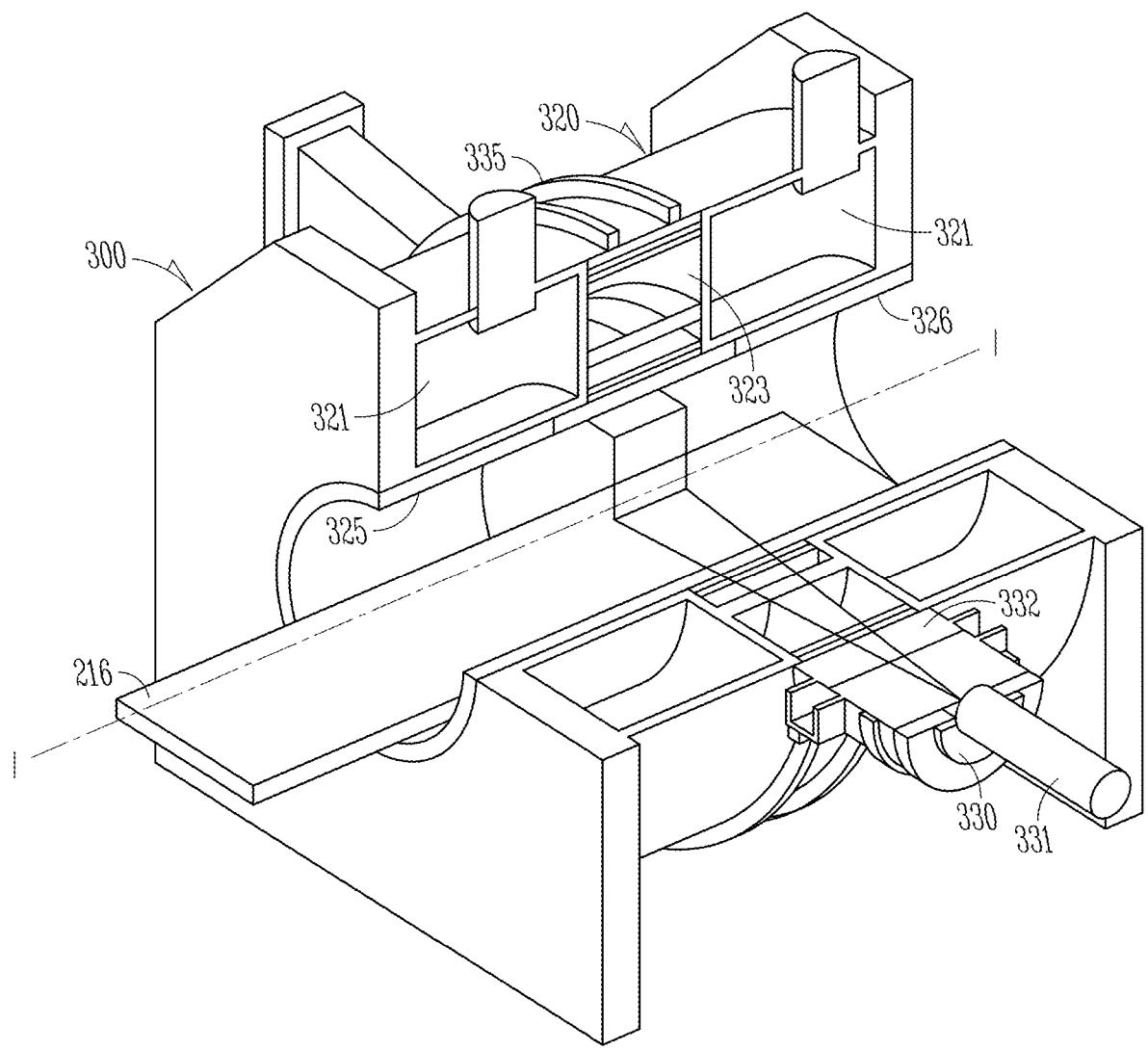
FIG. 3 illustrates a partially cut-away view of an exemplary system including a combined radiation therapy system and an imaging system, such as a nuclear MR imaging (MRI) system, according to some embodiments of the present disclosure.
Figure 4B:
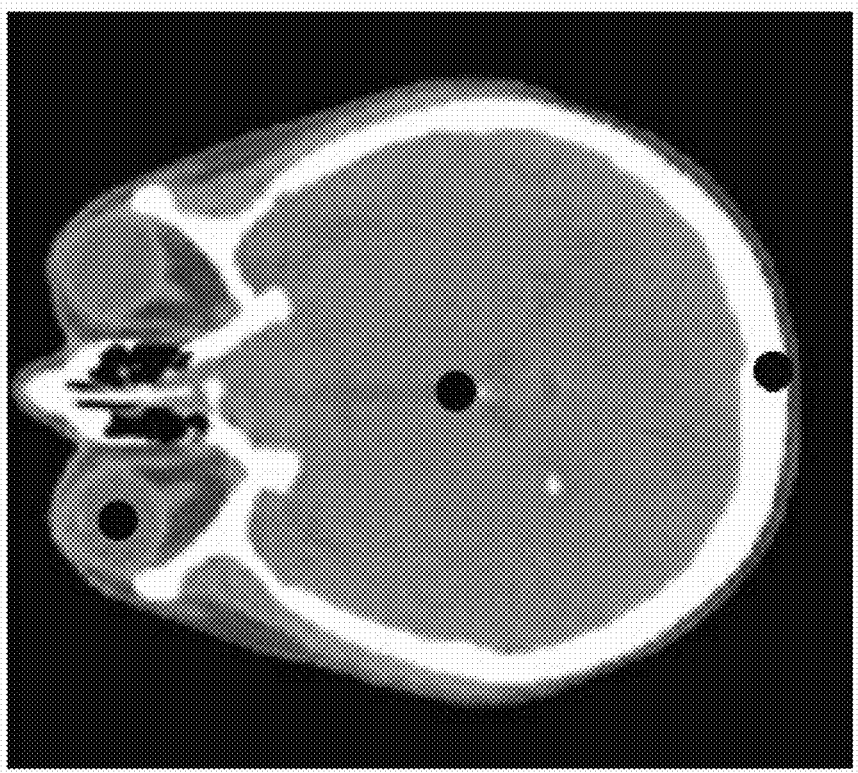
FIGS. 4A and 4B depict the differences between an exemplary MRI image and a corresponding CT image, respectively, according to some embodiments of the present disclosure.
Figure 4A:
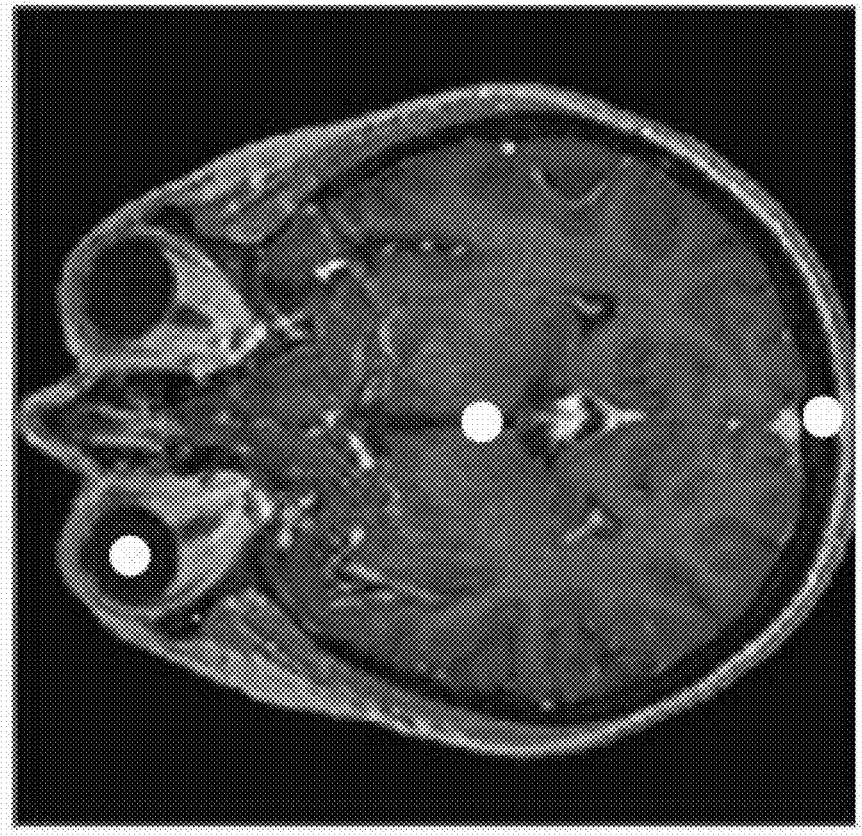

FIG. 3 depicts an exemplary radiation therapy system 300 that can include combining a radiation therapy device 202 and an imaging system, such as a nuclear MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first modality (e.g., MRI image shown in FIG. 4A) or destination images of a second modality (e.g., CT image shown in FIG. 4B).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In embodiments where magnet 321 can also include a central window 323 between coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Radiotherapy device 330 may include the radiation source 331, such as an X-ray source or a linac, and an MLC 332 (shown below in FIG. 5). Radiotherapy device 330 may be mounted on a chassis 335. One or more chassis motors (not shown) may rotate chassis 335 around couch 216 when couch 216 is inserted into the treatment area. In an embodiment, chassis 335 may be continuously rotatable around couch 216, when couch 216 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 216, image acquisition device 320, and radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnet 321, coils 325 and 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 illustrate generally illustrate embodiments of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

As discussed above, radiation therapy devices described by FIG. 2A, FIG. 2B, and FIG. 3 include an MLC for shaping, directing, or modulating an intensity of a radiation therapy beam to the specified target locus within the patient. FIG. 5 illustrates an exemplary MLC 332 that includes leaves 532A through 532J that can be automatically positioned to define an aperture approximating a tumor 540 cross section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates, such as comprising tungsten, with a long axis of the plates oriented parallel to a beam direction and having ends oriented orthogonally to the beam direction (as shown in the plane of the illustration of FIG. 2A). A "state" of the MLC 332 can be adjusted adaptively during a course of radiation therapy treatment, such as to establish a therapy beam that better approximates a shape or location of the tumor 540 or another target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as IMRT.

Figure 6:
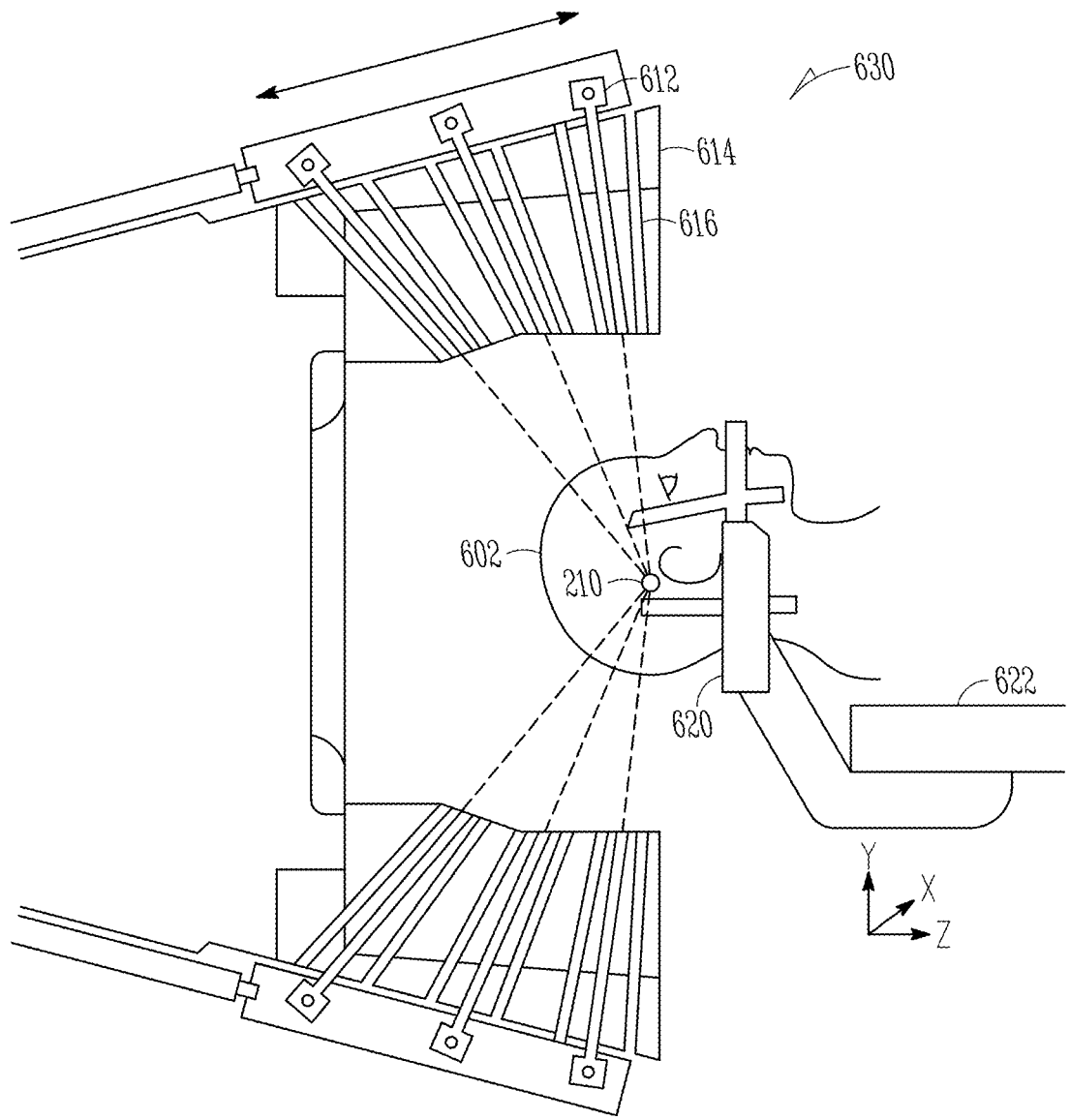
FIG. 6 illustrates an exemplary Gamma Knife radiation therapy system, according to some embodiments of the present disclosure.

FIG. 6 illustrates an embodiment of another type of radiotherapy device 630 (e.g., a Leksell Gamma Knife), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

Figure 7:
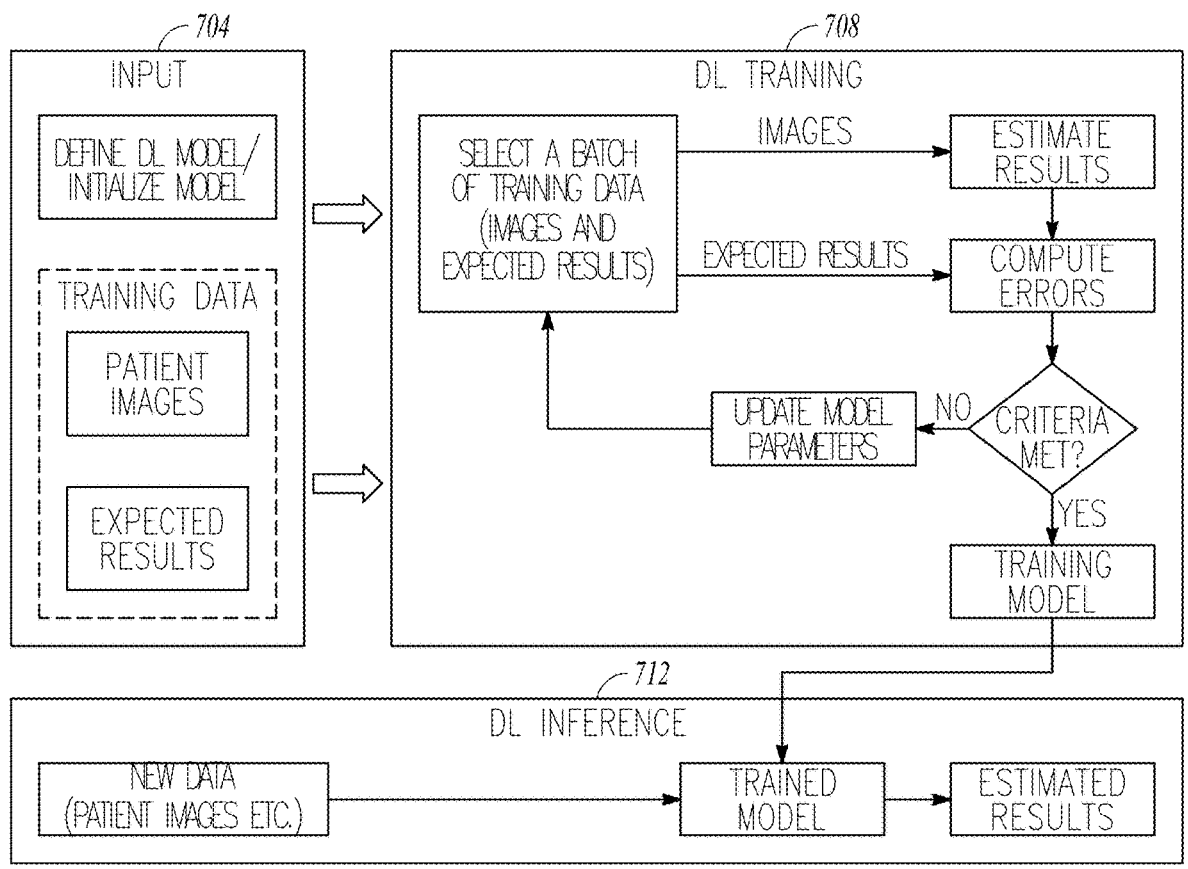
FIG. 7 illustrates an exemplary flow diagram for deep learning, according to some embodiments of the present disclosure.

FIG. 7 illustrates an exemplary flow diagram for deep learning, where a deep learning model (or a machine learning model), such as a deep convolutional neural network (DCNN), can be trained and used to determine a segmentation adapted to the anatomy displayed in the current fraction image. The segmentation can be used to produce or update a treatment plan or configure one or more radiotherapy treatment parameters.

Inputs 704 can include a defined deep learning model (which can include one or more sub-networks or one or more individual and independent machine learning models) having an initial set of values and training data. The training data can include patient images and expected results. The training data can also include data based on the patient images (e.g., images received across multiple treatment fractions), such as one or more of anatomy label maps or signed distance maps and/or contours of images (e.g., segmentations of the images) The training data can also include paired data sets, where each data set includes a first image (an image received at a first radiotherapy treatment fraction) of a patient anatomy, a segmentation (ground-truth segmentation) of the first image, a second image (an image received at a second radiotherapy treatment fraction that sequentially follows the first radiotherapy treatment fraction) of the same patient anatomy, and a corresponding segmentation of the second image. The training data can include multiple of these paired images for multiple patients.

The deep learning model can include one or more neural networks (referred to as sub-networks), such as a DCNN. The deep learning network can be trained on medical images and segmentations of the medical images. In one embodiment, the deep learning network is trained in an end-to-end manner in which all of the sub-networks are trained simultaneously by being applied to a same set or batch of training data and minimizing a set of cost functions. In another embodiment, one or more of the sub-networks of the DCNN are trained separately and independently in sequence by minimizing a set of cost functions associated with each particular sub-network.

The training medical images can include images of an anatomy, CT images, PET images, or MRI images across multiple treatment fractions. When trained, the deep learning network can produce a segmentation adapted to the anatomy displayed in the current fraction image. The expected results can include the segmentation adapted to the anatomy displayed in the current fraction image that can be used to compute a change in an amount of dose delivered to a target and/or movement of the target between time points when the images were captured, and such information can be used for defining the delivery of radiation treatment to a patient (e.g., to update the control points or machine parameters of a radiotherapy treatment device). The control points or machine parameters can include at least one gantry angle, at least one multi-leaf collimator leaf position, and at least one aperture weight or intensity.

During training of deep learning (DL) model 708, a batch of training data can be selected from the pairs of patient images and associated segmentations and expected results (e.g., the corresponding ground-truth segmentations) The selected training data can include at least a first image and segmentation of the first image captured at a first point in time (e.g., during a first treatment fraction) and at least a second image and corresponding segmentation captured at a second point in time (e.g., during a subsequent second treatment fraction). In the case of end-to-end training, the batch of training data can be processed by all of the sub-networks of the DL model 708 simultaneously. In this case, a set of cost functions is minimized, the set of cost functions including a term based on a difference between an estimated segmentation produced by the DL model 708 and the ground-truth segmentation of the image received during the second treatment fraction. The set of cost functions may also be a combination of individual cost functions that act on various network outputs, as discussed below. In the case individual and sequential training of the sub-networks, the same or different set of training data may be used to train each sub-network.

The deep learning model 708 can be applied to the selected pairs of images and corresponding segmentations to provide estimated results (e.g., estimated segmentations), which can then be compared to the expected results (e.g., ground truth segmentations) to compute a difference or deviation that can provide an indication of training errors. The errors can be used during a procedure called backpropagation to update the parameters of the deep learning network (e.g., layer node weights and biases of each or of certain sub-networks of the model 708), in order to reduce or minimize errors during subsequent trials. The errors can be compared to predetermined criteria, such as proceeding to a sustained minimum for a specified number of training iterations. If the errors do not satisfy the predetermined criteria, then model parameters of the deep learning model 708 can be updated using backpropagation, and another batch of training data can be selected from the other sets of training data (of the same patient or other patients) and expected results for another iteration of deep learning model training. If the errors satisfy the predetermined criteria, then the training can be ended, and the trained model 708 can then be used during a deep learning testing or inference stage 712 to estimate segmentations based on images received during one or more treatment fractions. The trained model 708 can receive new images of two treatment fractions (e.g., a previous fraction and a current fraction) and provide estimated results (e.g., the segmentation for the current fraction image).

After updating the parameters of the DCNN, the iteration index can be incremented by a value of one. The iteration index can correspond to a number of times that the parameters of the DCNN have been updated. Stopping criteria can be computed, and if the stopping criteria are satisfied, then the DCNN model can be saved in a memory, such as the memory device 116 of image processing device 112, and the training can be halted. If the stopping criteria are not satisfied, then the training can continue by obtaining another batch of training images from the same training subject or another training subject. In an embodiment, the stopping criteria can include a value of the iteration index (e.g., the stopping criteria can include whether the iteration index is greater than or equal to a determined maximum number of iterations). In an embodiment, the stopping criteria can include an accuracy of the output segmentation (e.g., the stopping criteria can include whether the difference between the output segmentation and the ground-truth segmentation in the batch of training data is smaller than a threshold).

After the DL model 708 is trained, a pair of medical images of an anatomy can be received from an image acquisition device, such as image acquisition device 132. The pair of medical images can include an image captured or generated at a first point in time (e.g., during a first treatment fraction) along with a segmentation of the image captured at the first point in time and an image captured or generated at a second point in time (e.g., during a second treatment fraction in real-time during treatment of a patient). A trained DCNN model can be received from a network, such as the network 120, or from a memory, such as the memory device 116 of image processing device 112. The trained DCNN can be used to determine the estimated segmentation of the image captured at the second point in time based on the image and corresponding segmentation captured at the first point in time.

Figure 8A:
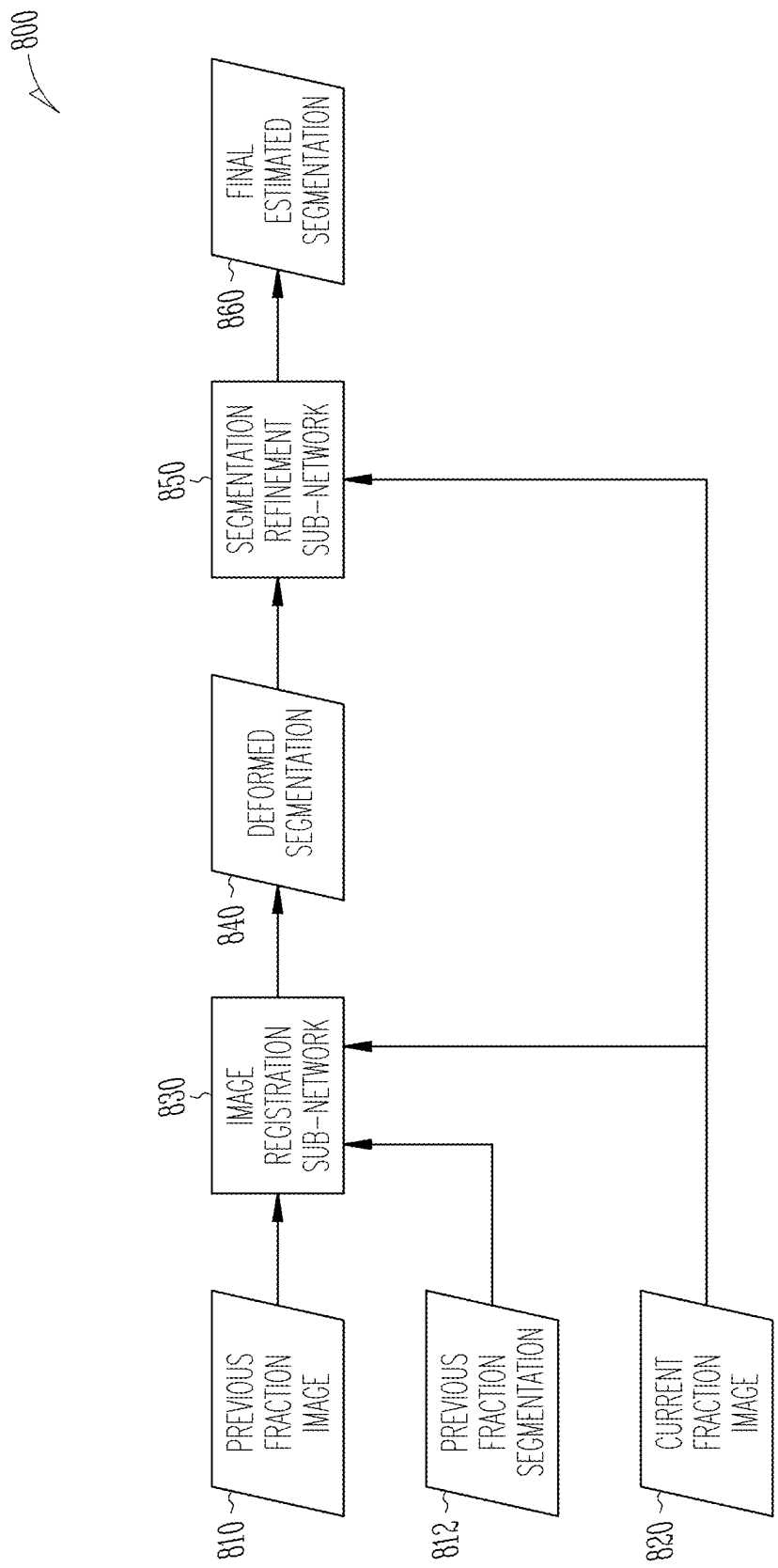
FIGS. 8A, 8B, and 9 illustrate exemplary flow diagrams for estimating a refined segmentation for an image, according to some embodiments of the present disclosure.
Figure 8B:
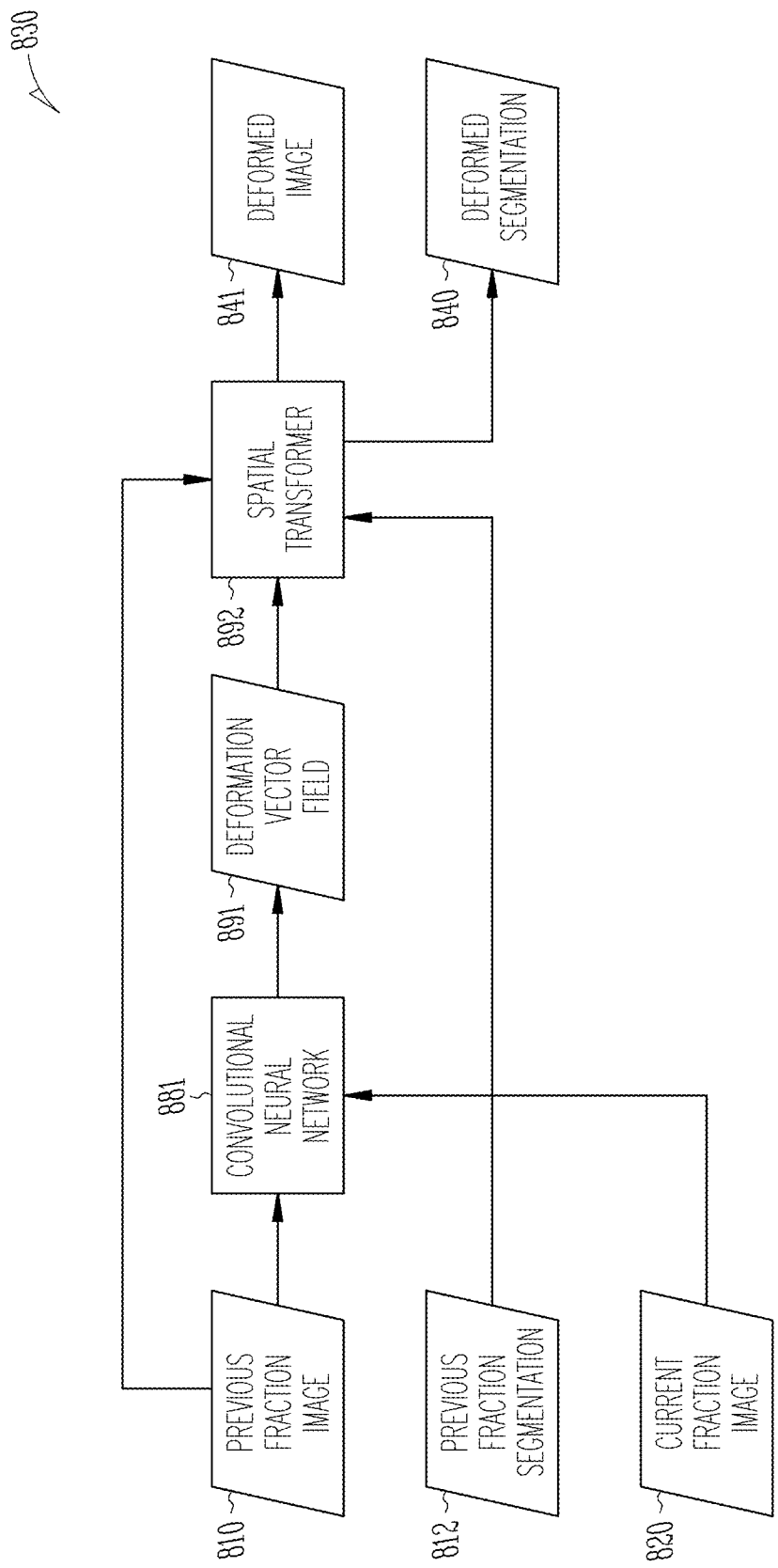
Figure 9:
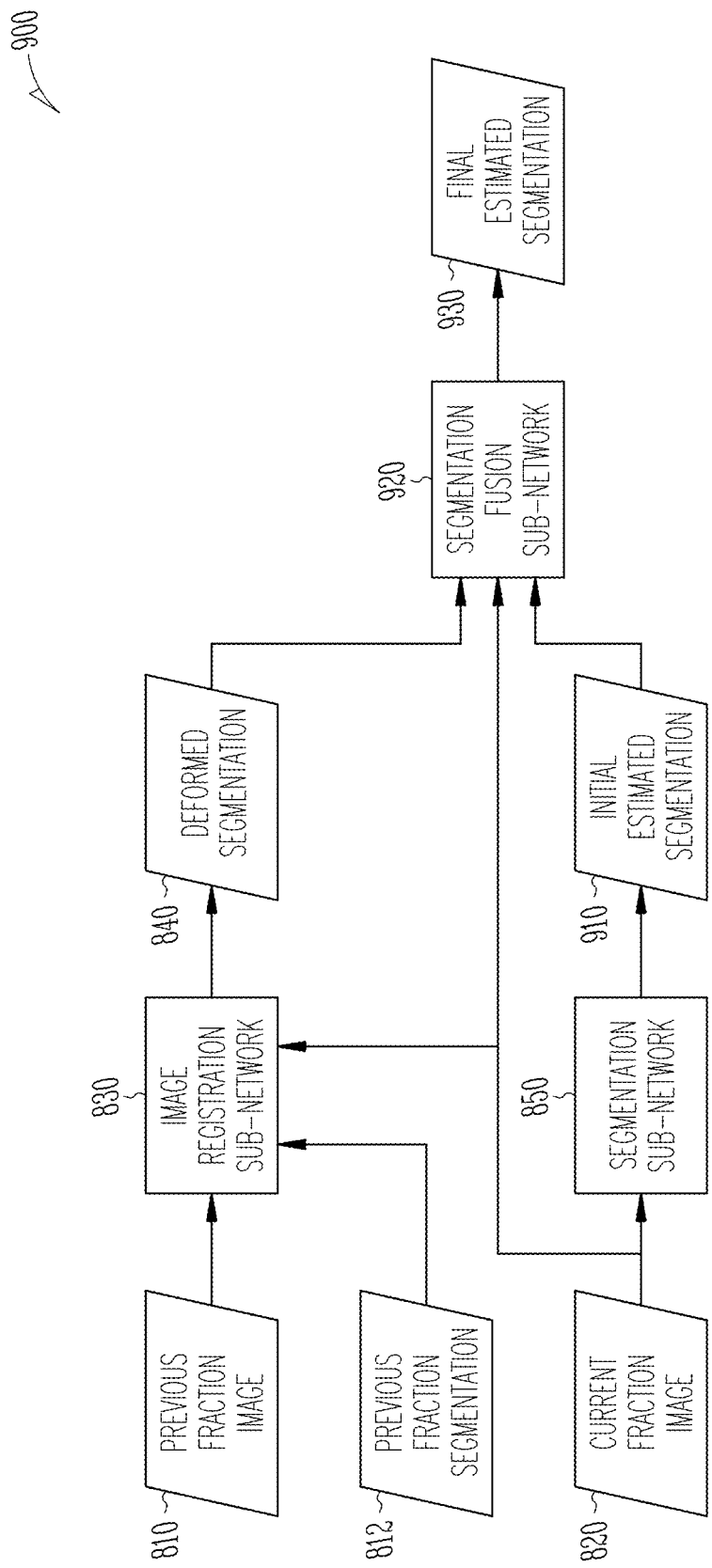

FIGS. 8A, 8B, and 9 illustrate exemplary flow diagrams for estimating a refined segmentation for an image, according to some embodiments of the present disclosure.

For example, the flow diagram 800 depicts the model 708 (e.g., an image registration sub-network 830) receiving a previous fraction image 810 and corresponding previous fraction segmentation 812. The model 708 also receives a current fraction image 820. During training, these images are received from a batch of training data. After training the model 708, these images are received from results of applying radiotherapy treatment to a patient, such as in real-time.

The previous fraction image 810 and corresponding previous fraction segmentation 812, and the current fraction image 820 are applied to a first sub-network of the model 708. The first sub-network may be an image registration sub-network 830. In some implementations, prior to applying the previous fraction image 810 and corresponding previous fraction segmentation 812, and the current fraction image 820 to the image registration sub-network 830, the previous fraction image 810 can be pre-processed with the current fraction image 820 to coarsely align the images (e.g., using another image registration technique). In some implementations, one or more contours associated with the previous fraction image 820 are received. The one or more contours are converted to label maps or a binary segmentation to generate the previous fraction segmentation 812.

The image registration sub-network 830 produces a deformed segmentation 840 that adapts the previous fraction segmentation 812 to the anatomy of the subject depicted in the current fraction image 820. Specifically, the previous fraction image 810 and the current fraction image 820 are first processed by the image registration sub-network 830, which produces an estimated deformation vector field (DVF), which maps corresponding voxels or pixels from the previous fraction image 810 to the current fraction image 820. The previous fraction segmentation 812 is then resampled using the same estimated DVF onto the current fraction image 820, producing a segmentation 840 deformed to fit the anatomy of the current fraction image 820. This estimated initial segmentation 840 is then provided as input to a second sub-network of the model 708 (e.g., a segmentation refinement sub-network 850), along with the current fraction image 820. The segmentation refinement sub-network 850 produces the final estimated segmentation 860 for the current fraction.

In other possible embodiments, alternative network architectures may instead be used. For example, the image registration sub-network 830 may be omitted from the model 708, in which case a single segmentation network with two inputs (e.g., the previous fraction segmentation and the current fraction image) or three inputs (e.g., the previous fraction image and corresponding segmentation, and the current fraction image) may be used to directly estimate the final adapted segmentation 860. In other embodiments, the segmentation refinement sub-network 860 may be omitted from the model 708 instead of omitting the image registration sub-network 830. In this case, the deformed segmentation (e.g., the output of the image registration sub-network 830) is provided as the final adapted segmentation 860.

As shown in FIG. 8B, a detailed illustration and flow diagram of the image registration sub-network 830 is provided. Similar components of the flow diagram shown in FIG. 8B as those shown in FIG. 8A are similarly labeled. The image registration sub-network 830 includes a convolutional neural network (CNN) 881 that receives the previous fraction image 810, the previous fraction segmentation 812, and the current fraction image 820.

The task of the image registration sub-network 830 is to estimate a DVF 891 which maps corresponding voxels or pixels of the previous fraction image 810 to the current fraction image 820 (e.g., the daily MR image). As such, the input to the image registration sub-network 830 includes both the previous fraction image 810 and the current image 820, which may be concatenated along the channel dimension, producing a single extra-dimensional sample. Several network architectures may be used to perform the deformable registration task. In one embodiment, an encoder/decoder (e.g., U-Net style) architecture is used. Regardless of the specific architecture, the output of the encoder/decoder network is a DVF 891 which is passed to a spatial transformer 892. The spatial transformer 892 resamples the previous fraction image 810 and previous fraction segmentation 812 to produce an image/segmentation pair (e.g., a deformed image 841 and deformed segmentation 840), which is better aligned with the current fraction image 820. The deformed image 841 may not be used by the segmentation refinement sub-network 850 but may be used in training to train and optimize the image registration sub-network 830.

The image registration sub-network 830 can be trained together or simultaneously with other sub-networks of the model 708 or separately and independently of other sub-networks. In some embodiments, the image registration sub-network 830 is trained prior to training the segmentation refinement sub-network 850.

To train the image registration sub-network 830, at each training iteration, a batch of training data that includes a 4-tuple is generated and received (e.g., from storage). The batch of training data is used to optimize the network parameters using stochastic gradient descent (or other adaptive alternatives) with respect to the minimization of one or more specified loss functions. The training 4-tuple includes four corresponding samples, each drawn from the same training subject and physical coordinates: (1) sample drawn from the previous fraction image; (2) the ground truth segmentation corresponding to sample (1); (3) a sample drawn from the current fraction image; and (4) the ground truth segmentation corresponding to sample (3). In practice, acquiring multiple fractions of labelled data for many subjects may be burdensome, and multiple synthetic fractions may instead be generated by applying either user-specified or automatically generated transformations to any available labelled fractions. In some cases, standard data augmentation techniques may be used to artificially increase the diversity of the training samples (e.g., using random transforms), reducing the threat of overfitting.

At each iteration, the sample drawn from the previous fraction image and its ground truth segmentation and a sample drawn from the current fraction image are input to the image registration sub-network 830. The image registration sub-network 830 estimates or produces a DVF that maps voxels or pixels from the previous fraction image to the current fraction image. The DVF is used by a spatial transformer 892 to generate a deformed image 841 and a deformed segmentation 840. For example, the previous fraction image 810 can be adjusted based on the DVF to deform the previous fraction image 810 to generate the deformed image 841. Similarly, the previous fraction segmentation 812 can be adjusted based on the DVF to deform the previous fraction segmentation 812 to generate the deformed segmentation 840.

One or more cost functions can be computed alone or in combination representing image-based metrics and/or segmentation-based metrics. To compute the cost function representing the image-based metric, a difference or deviation between the deformed image 841 and the actual current fraction image 820 is computed or determined (e.g., using the sum of squared differences (SSD) or the negative local cross-correlation on the sample intensities). Based on the difference or deviation, parameters of the image registration sub-network 830 are updated to minimize the difference or deviation when a subsequent batch of data is processed. Such a cost function may be suitable for cases in which both the previous fraction image and the current fraction image have the same or sufficiently similar contrast. In cases where the contrast differs, more robust image-based metrics may be used (e.g., SSD on MIND features instead of SSD on the sample intensities, or image translation methods may be used to convert the inter-modality registration problem into an intra-modality). To compute the cost function representing segmentation-based metrics, which are inherently contrast-independent, a difference or deviation between the deformed segmentation 840 and the actual current fraction segmentation (e.g., the ground-truth segmentation of the current fraction image) is computed or determined (e.g., using cross-entropy or Dice overlap losses). Based on the difference or deviation, parameters of the image registration sub-network 830 are updated to minimize the difference or deviation when a subsequent batch of data is processed. The image-based and segmentation-based metrics may be combined and weighted in some implementations to update parameters of the image registration sub-network 830. In some cases, an additional loss function is provided and computed to promote the generation of smooth DVFs; such a metric could be based on, for example, the sum of the norms of the gradients of the DVF with respect to each orthogonal spatial dimension.

Referring back to FIG. 8A, the segmentation refinement sub-network 850 can also be trained together (in an end-to-end fashion) with the image registration sub-network 830 or separately after the image registration sub-network 830 has been trained. The segmentation refinement sub-network 850 can also be implemented as an encoder/decoder (e.g., U-Net style) architecture. To train the segmentation refinement sub-network 850, the deformed segmentation 840 is received from the image registration sub-network 830 (e.g., at each iteration or multiple deformed segmentations 840 each associated with a corresponding current fraction image 820 of the training batch can be generated and stored). The segmentation refinement sub-network 850 computes a cost function that represents a difference or deviation between the deformed segmentation 840 of a current fraction image 820 and the ground truth segmentation of the current fraction image 820 in the training batch. Standard segmentation-based metrics may be used in the cost function (e.g., cross-entropy or Dice overlap losses). Based on the difference or deviation, parameters of the segmentation refinement sub-network 850 are updated to minimize the difference or deviation when a subsequent batch of data is processed.

In the case of training the segmentation refinement sub-network 850 together with the image registration sub-network 830 in an end-to-end manner, a combined cost function can be computed. The combined cost function can include one or more components including an image-based metric, one or more segmentation-based metrics, and/or a smooth DVF based metric. These components can be weighted and used to update one or more parameters of the various sub-networks of the model 708.

In some embodiments, the model 708 includes a third sub-network (e.g., a segmentation fusion sub-network). The flow diagram 900 (FIG. 9) represents the process for training and using the model 708 to generate a refined segmentation according to such embodiments. Namely, rather than providing the deformed segmentation from the image registration sub-network 830 to the segmentation sub-network 850, each of the image registration sub-network 830 and the segmentation sub-network 850 produces its own estimated segmentation for the current fraction image. The separately produced segmentations of the current fraction image 820 are provided together with the current fraction image 820 to the third sub-network (the segmentation fusion sub-network 920) which combines the two segmentations to generate the refined segmentation 930.

In this embodiment, shown in FIG. 9, the model 708 receives the previous fraction image 810 and corresponding previous fraction segmentation 812 and also receives the current fraction image 820. During training, these images are received from a batch of training data. After training the model 708, these images are received from results of applying radiotherapy treatment to a patient, such as in real-time.

The model 708 applies the image registration sub-network 830 to the previous fraction image 810 and corresponding previous fraction segmentation 812 and also receives the current fraction image 820 to generate the deformed segmentation 840 (e.g., a first segmentation for the current fraction image 820). The image registration sub-network 830 can be trained in the same manner as previously discussed in connection with FIG. 8B Separately, and in parallel with the image registration sub-network 830 being applied to the previous fraction image 810 and corresponding previous fraction segmentation 812 and the current fraction image 820 to generate the deformed segmentation 840 the model 708, the model 708 applies the segmentation sub-network 850 to the current fraction image 820. This produces a second segmentation 910 for the current fraction image 820. The segmentation sub-network 850 can be trained in the same manner as discussed above together with or separately from the image registration sub-network 830 (e.g., after training the image registration sub-network 830).

The first segmentation (e.g., the deformed segmentation 840) produced by the image registration sub-network 830 and the second segmentation 910 produced by the segmentation sub-network 850 and the current fraction image 820 are provided to the segmentation fusion sub-network 920. The segmentation fusion sub-network 920 can also be implemented as an encoder/decoder (e.g., U-Net style) architecture. The segmentation fusion sub-network 920 generates a refined segmentation 930 based on this input data. To train the segmentation fusion sub-network 920, at each iteration, a cost function is computed that represents a difference or deviation between a refined segmentation produced by the segmentation fusion sub-network 920 and the ground truth segmentation of the current fraction image 820. Parameters of the segmentation fusion sub-network 920 are updated based on the difference or deviation. The segmentation fusion sub-network 920 can be trained together with the image registration sub-network 830 and the segmentation sub-network 850 or separately and sequentially after training the image registration sub-network 830 and the segmentation sub-network 850.

Figure 10A:
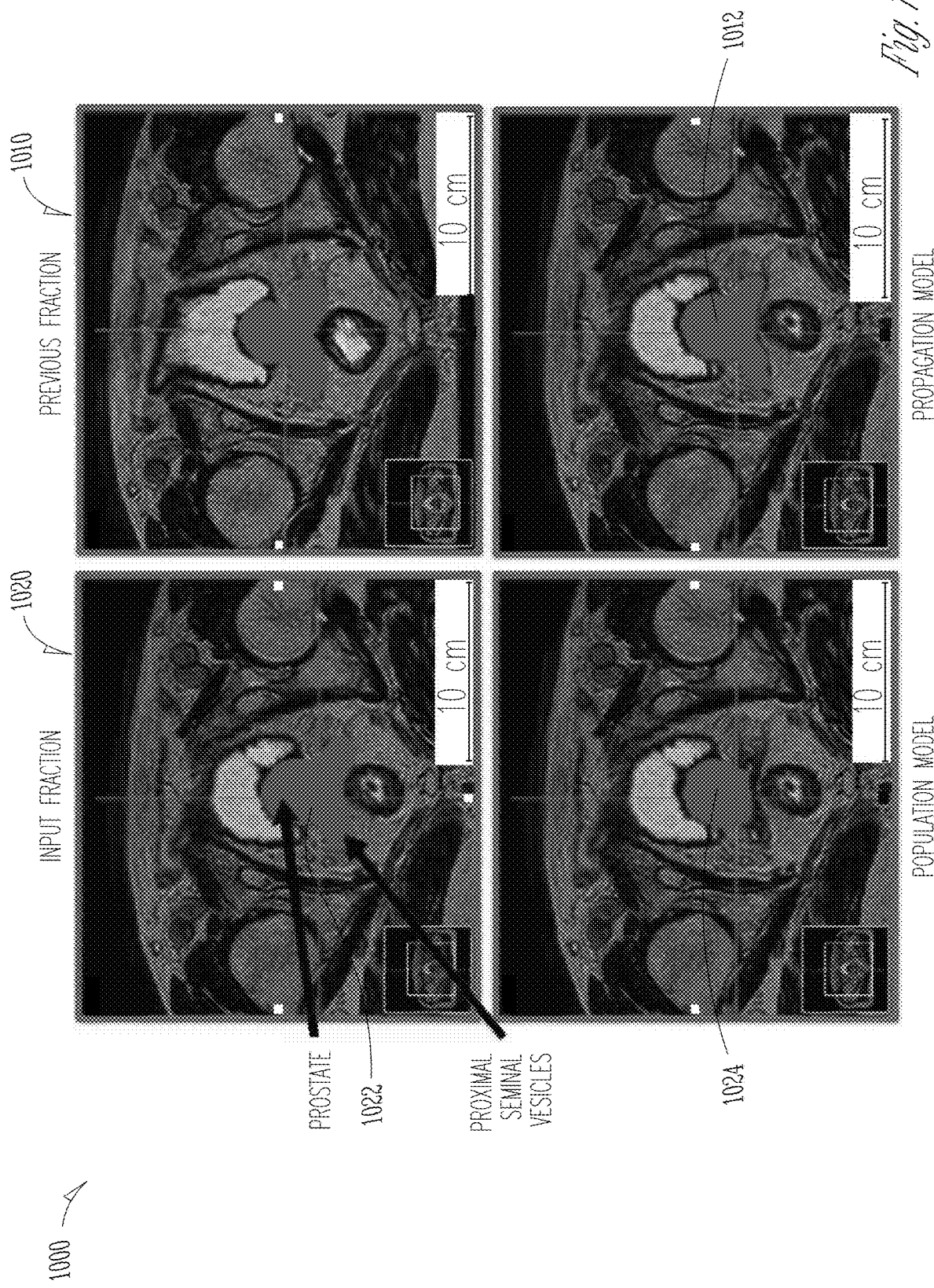
FIGS. 10A and 10B depict the differences between a segmentation for an image produced by a population model and a segmentation produced by the propagation model, according to some embodiments of the present disclosure.
Figure 10B:
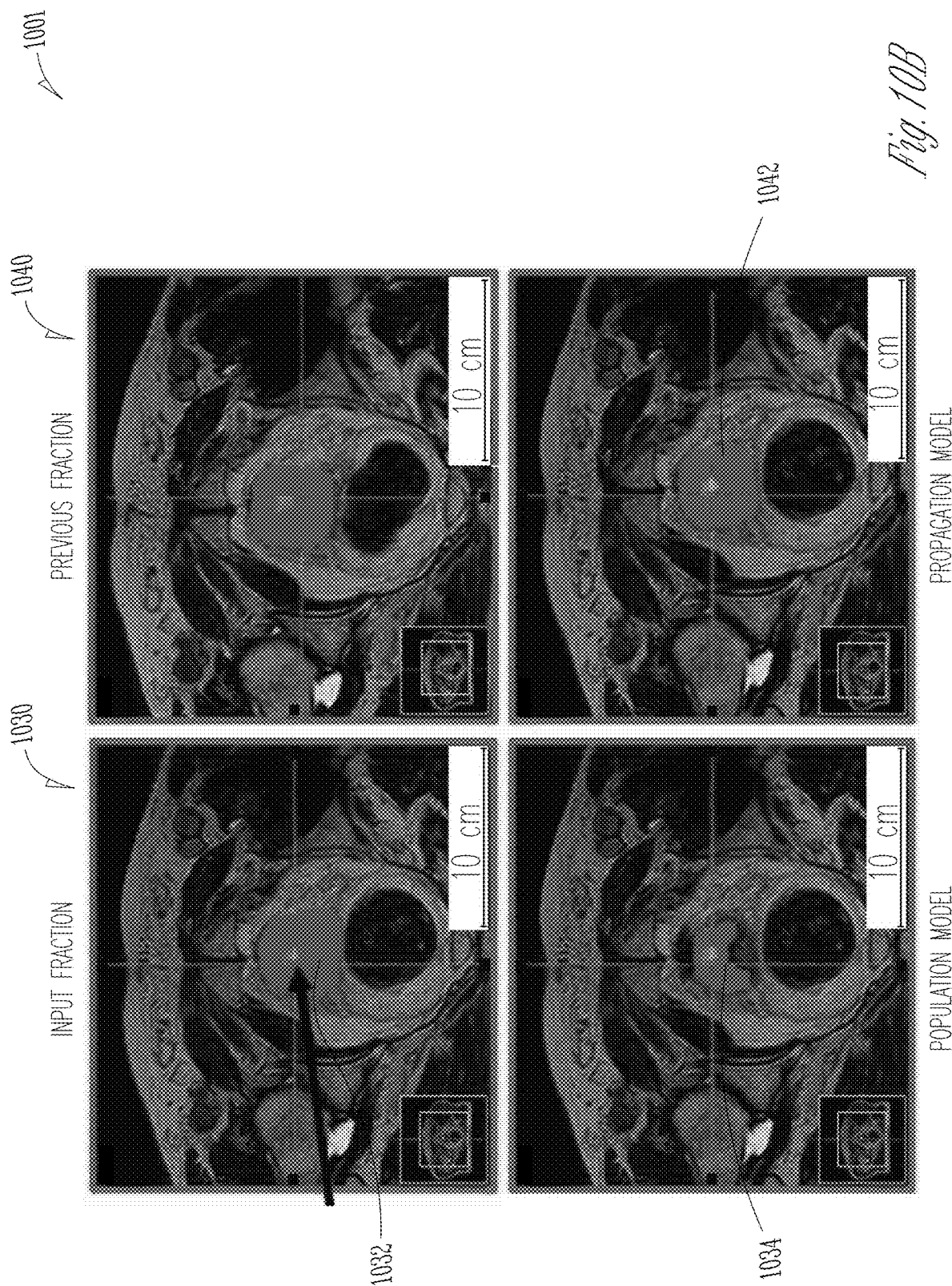

FIGS. 10A and 10B depict the differences between a segmentation for an image produced by a population model and a segmentation produced by the propagation model, according to some embodiments of the present disclosure. For example, as shown in example 1000, a previous fraction image 1010 is shown and a current fraction image 1020 is shown A ground truth segmentation cumulative target volume (CTV) 1022 is overlaid and shown in red for the current fraction image 1020. For low-risk patients, the CTV usually contains the prostate with a small added margin. However, for some higher-risk patients, this patient included, the CTV definition may additionally include the proximal seminal vesicles.

A contour 1024 for the current fraction image 1020 is shown that is generated based on a typical population model. The trained model 708 is applied to the previous fraction image 1010 and the current fraction image 1020 together with the segmentation of the previous fraction image 1010. A refined segmentation 1012 is shown that is output by the trained model 708. The population-trained model tends to produce an "average" CTV contour 1024 which includes very little of the proximal seminal vesicles. On the other hand, by using the previous fraction image 1010 to provide cues about contour style, the trained model 708 correctly produced a CTV (refined segmentation 1012) with a more consistent style (e.g., a contour including the proximal vesicles). Namely, the refined segmentation 1012 produced by the trained model 708 matches better the ground truth segmentation CTV 1022 than the CTV contour 1024 produced by the population model.

As another example, as shown in example 1001, a previous fraction image 1040 is shown and a current fraction image 1030 is shown. A ground truth segmentation CTV 1032 is overlaid and shown in red for the current fraction image 1030.

Here, the patient has what appears to be a damaged and enlarged prostatic urethra, which appears as a bright white spot in the middle of the prostate. Since this case is not represented in the population training data, the population model has difficulty with this case, as shown in the output segmentation 1034. On the other hand, by providing the trained model 708 with a reference fraction (e.g., the previous fraction image 1040), the resultant segmentation 1042 is much closer to the ground truth segmentation CTV 1032.

Figure 11:
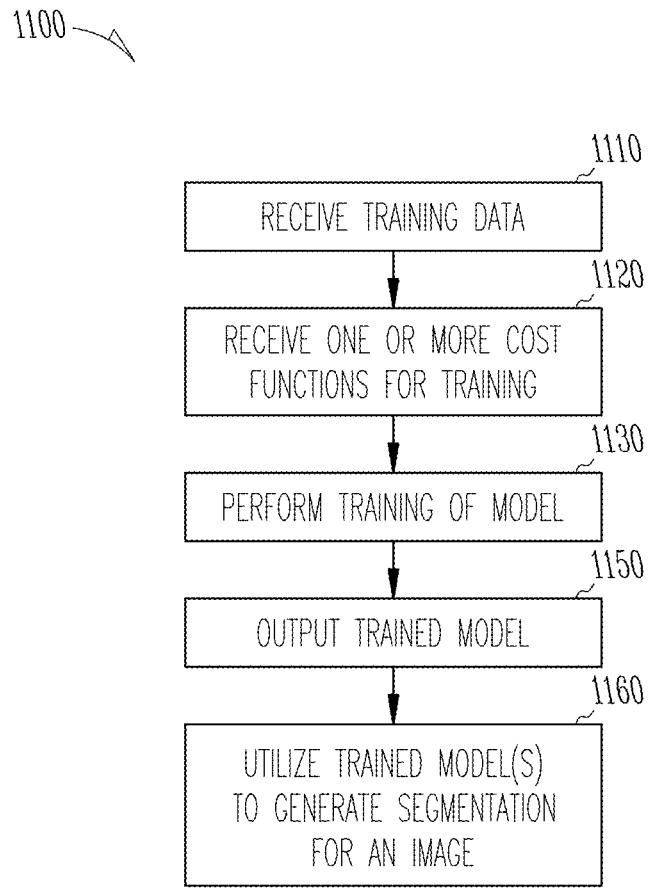
FIG. 11 illustrates an exemplary data flow for training and use of a machine learning model to generate a refined segmentation, according to some embodiments of the present disclosure.

FIG. 11 is a flowchart illustrating example operations of the image processing device 112 in performing process 1100, according to example embodiments. The process 1100 may be embodied in computer-readable instructions for execution by one or more processors such that the operations of the process 1100 may be performed in part or in whole by the functional components of the image processing device 112; accordingly, the process 1100 is described below by way of example with reference thereto. However, in other embodiments, at least some of the operations of the process 1100 may be deployed on various other hardware configurations. The process 1100 is therefore not intended to be limited to the image processing device 112 and can be implemented in whole, or in part, by any other component. Some or all of the operations of process 1100 can be in parallel, out of order, or entirely omitted.

At operation 1110, image processing device 112 receives training data. For example, image processing device 112 receives training data, which may include paired training data sets (e.g., input-output training pairs).

At operation 1120, image processing device 112 receives one or more cost functions for training the model.

At operation 1130, image processing device 112 performs training of the model based on the received training data and one or more cost functions.

At operation 1150, image processing device 112 outputs the trained model. For example, image processing device 112 outputs the trained model to operate on a new set of images to generate a refined segmentation.

At operation 1160, image processing device 112 utilizes the trained model to generate a refined segmentation for a current treatment fraction image.

Figure 12A:
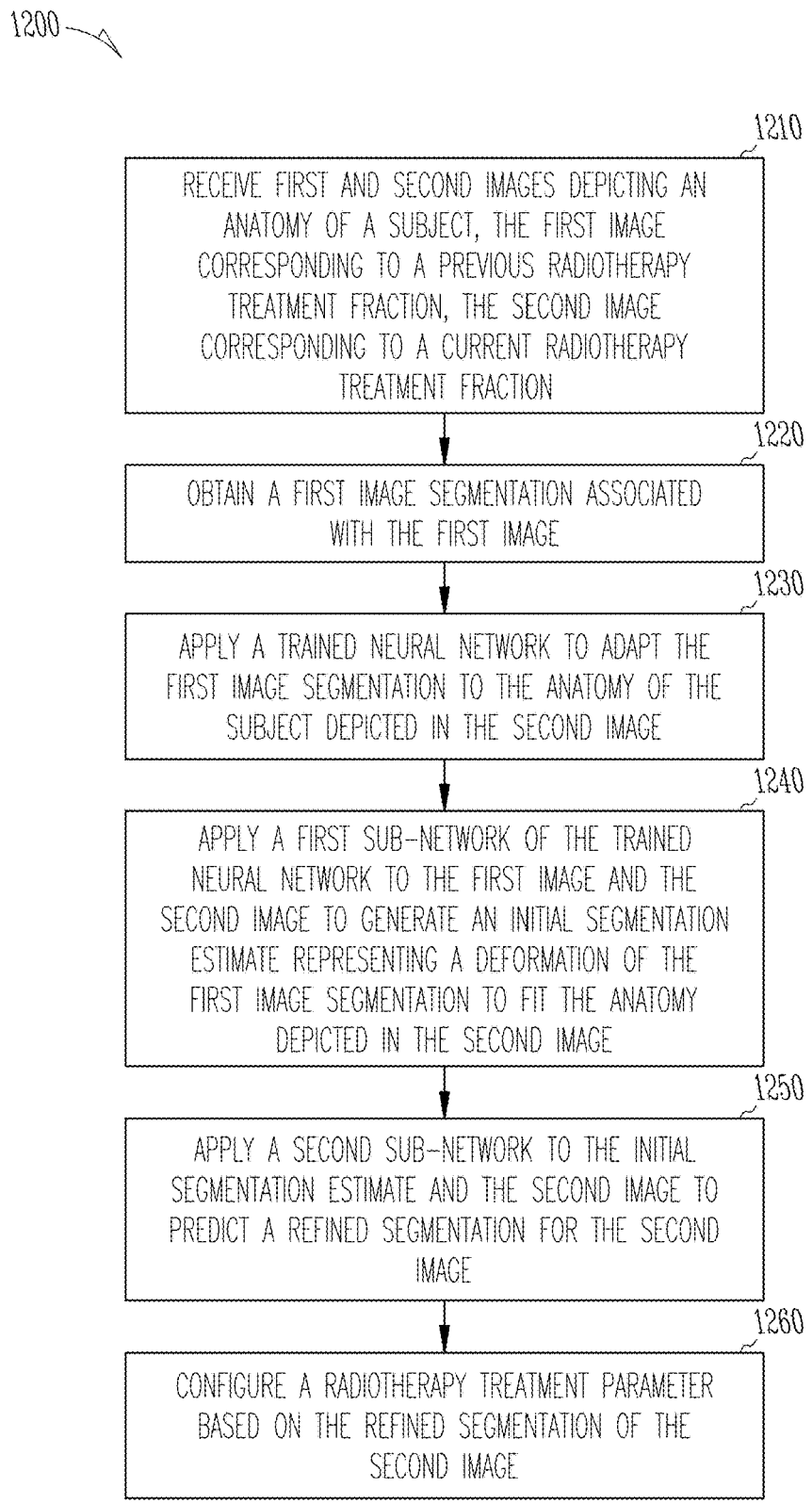
FIGS. 12A and 12B illustrate methods for using trained deep learning to generate a refined segmentation, according to some embodiments of the present disclosure.

FIG. 12A is a flowchart illustrating example operations of the image processing device 112 in performing process 1200, according to example embodiments. The process 1200 may be embodied in computer-readable instructions for execution by one or more processors such that the operations of the process 1200 may be performed in part or in whole by the functional components of the image processing device 112, accordingly, the process 1200 is described below by way of example with reference thereto. However, in other embodiments, at least some of the operations of the process 1200 may be deployed on various other hardware configurations. The process 1200 is therefore not intended to be limited to the image processing device 112 and can be implemented in whole, or in part, by any other component. Some or all of the operations of process 1200 can be in parallel, out of order, or entirely omitted.

At operation 1210, image processing device 112 receives first and second images depicting an anatomy of a subject, the first image corresponding to a previous radiotherapy treatment fraction and the second image corresponding to a current radiotherapy treatment fraction.

At operation 1220, image processing device 112 obtains a first image segmentation associated with the first image.

At operation 1230, image processing device 112 applies a trained neural network to adapt the first image segmentation to the anatomy of the subject depicted in the second image.

At operation 1240, image processing device 112 applies a first sub-network of the trained neural network to the first image and the second image to generate an initial segmentation estimate representing a deformation of the first image segmentation to fit the anatomy depicted in the second image, the first sub-network being trained to establish a relationship between a plurality of previous treatment fraction images and subsequently obtained treatment fraction images.

At operation 1250, image processing device 112 applies a second sub-network to the initial segmentation estimate and the second image to estimate a refined segmentation for the second image, the second sub-network being trained to establish a relationship between a plurality of initial segmentation estimates of a plurality of current fraction images and ground truth segmentations of the plurality of current fraction images.

At operation 1260, image processing device 112 configures a radiotherapy treatment parameter based on the refined segmentation of the second image.

Figure 12B:
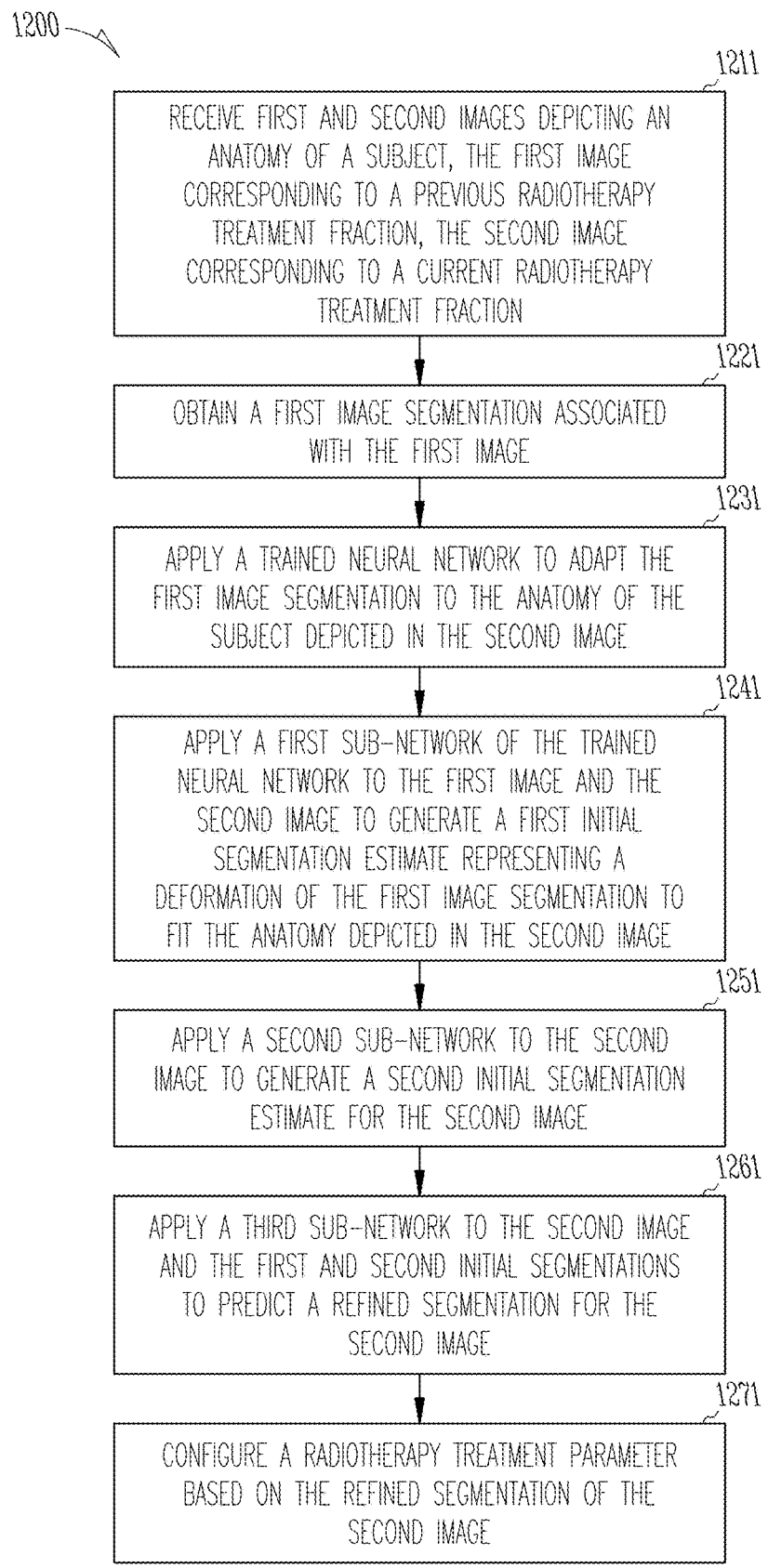

FIG. 12B is a flowchart illustrating example operations of the image processing device 112 in performing process 1201, according to example embodiments. The process 1201 may be embodied in computer-readable instructions for execution by one or more processors such that the operations of the process 1201 may be performed in part or in whole by the functional components of the image processing device 112; accordingly, the process 1201 is described below by way of example with reference thereto. However, in other embodiments, at least some of the operations of the process 1201 may be deployed on various other hardware configurations. The process 1201 is therefore not intended to be limited to the image processing device 112 and can be implemented in whole, or in part, by any other component. Some or all of the operations of process 1201 can be in parallel, out of order, or entirely omitted.

At operation 1211, image processing device 112 receives first and second images depicting an anatomy of a subject, the first image corresponding to a previous radiotherapy treatment fraction, the second image corresponding to a current radiotherapy treatment fraction.

At operation 1221, image processing device 112 obtains a first image segmentation associated with the first image.

At operation 1231, image processing device 112 applies a trained neural network to adapt the first image segmentation to the anatomy of the subject depicted in the second image.

At operation 1241, image processing device 112 applies a first sub-network of the trained neural network to the first image and the second image to generate a first initial segmentation estimate representing a deformation of the first image segmentation to fit the anatomy depicted in the second image, the first sub-network being trained to establish a relationship between a plurality of previous treatment fraction images and subsequently obtained treatment fraction images.

At operation 1251, image processing device 112 applies a second sub-network to the second image to generate a second initial segmentation estimate for the second image, the second sub-network being trained to establish a relationship between a plurality of current treatment fraction images and corresponding ground truth segmentations.

At operation 1261, image processing device 112 applies a third sub-network to the second image and the first and second initial segmentations to estimate a refined segmentation for the second image, the third sub-network being trained to establish a relationship between a plurality of pairs of initial segmentation estimates and the corresponding ground truth segmentations.

At operation 1271, image processing device 112 configures a radiotherapy treatment parameter based on the refined segmentation of the second image.

Figure 13:
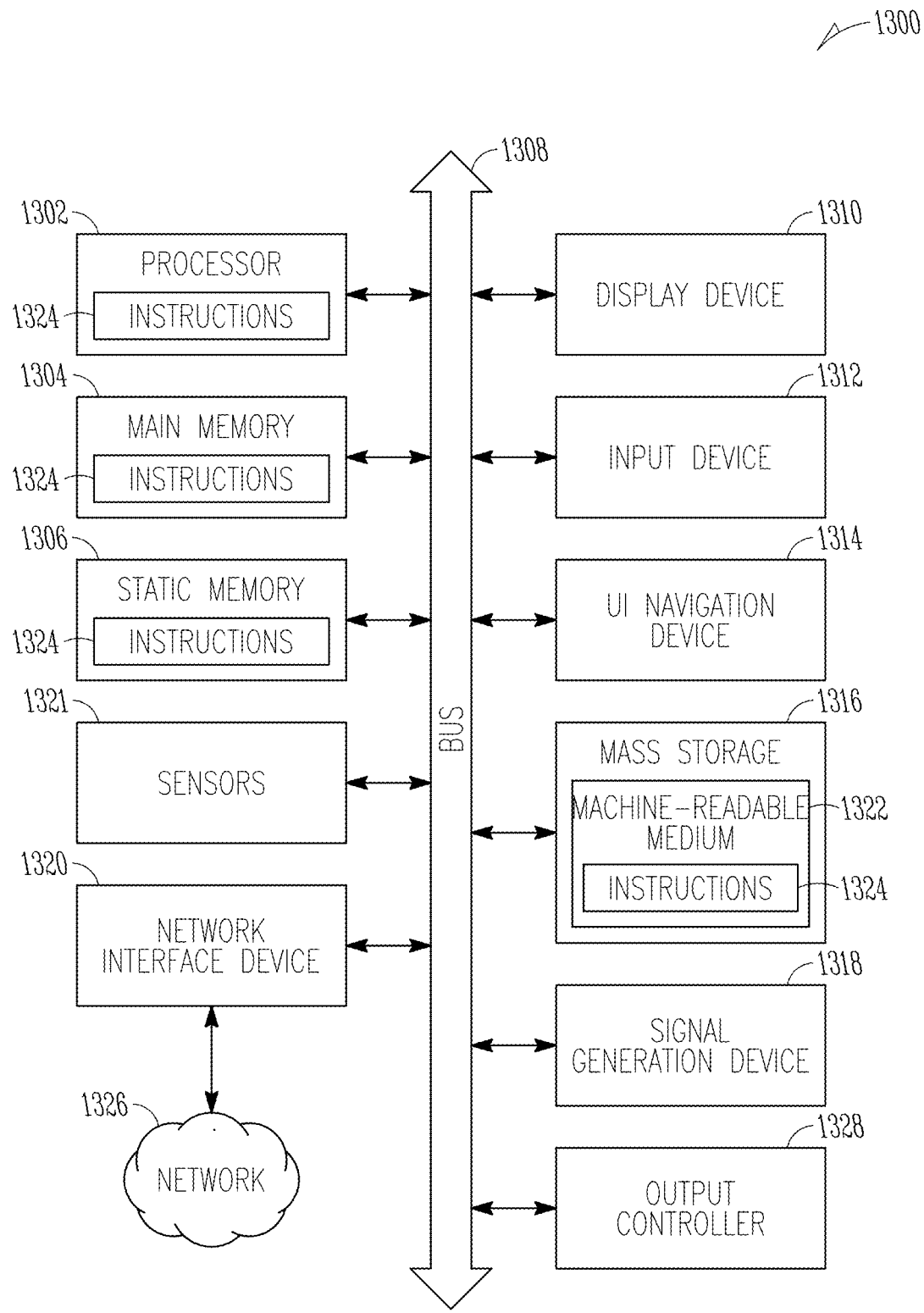
FIG. 13 illustrates an exemplary block diagram of a machine on which one or more of the methods as discussed herein can be implemented.

FIG. 13 illustrates a block diagram of an embodiment of a machine 1300 on which one or more of the methods as discussed herein can be implemented. In one or more embodiments, one or more items of the image processing device 112 can be implemented by the machine 1300. In alternative embodiments, the machine 1300 operates as a standalone device or may be connected (e.g., networked) to other machines. In one or more embodiments, the image processing device 112 can include one or more of the items of the machine 1300. In a networked deployment, the machine 1300 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform an, one or more of the methodologies discussed herein.

The example machine 1300 includes processing circuitry 1302 (e.g., a CPU, a GPU, an ASIC, circuitry, such as one or more transistors, resistors, capacitors, inductors, diodes, logic gates, multiplexers, buffers, modulators, demodulators, radios (e.g., transmit or receive radios or transceivers), sensors 1321 (e.g., a transducer that converts one form of energy (e.g., light, heat, electrical, mechanical, or other energy) to another form of energy), or the like, or a combination thereof), a main memory 1304 and a static memory 1306, which communicate with each other via a bus 1308. The machine 1300 (e.g., computer system) may further include a video display unit 1310 (e.g., a liquid crystal display (LCD) or a cathode ray tube (CRT)). The machine 1300 also includes an alphanumeric input device 1312 (e.g., a keyboard), a user interface (UI) navigation device 1314 (e.g., a mouse), a disk drive or mass storage unit 1316, a signal generation device 1318 (e.g., a speaker), and a network interface device 1320.

The disk drive or mass storage unit 1316 includes a machine-readable medium 1322 on which is stored one or more sets of instructions and data structures (e.g., software) 1324 embodying or utilized by any one or more of the methodologies or functions described herein. The instructions 1324 may also reside, completely or at least partially, within the main memory 1304 and/or within the processor 1302 during execution thereof by the machine 1300, the main memory 1304 and the processor 1302 also constituting machine-readable media.

The machine 1300 as illustrated includes an output controller 1328. The output controller 1328 manages data flow to/from the machine 1300. The output controller 1328 is sometimes called a device controller, with software that directly interacts with the output controller 1328 being called a device driver.

While the machine-readable medium 1322 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks, magneto-optical disks; and CD-ROM and DVD-ROM disks.

The instructions 1324 may further be transmitted or received over a communications network 1326 using a transmission medium. The instructions 1324 may be transmitted using the network interface device 1320 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMs, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., ROMs), EPROMS, EEPROMS, or any type of media suitable for storing electronic instructions, and the like. Such computer readable storage medium coupled to a computer system bus to be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, Compute Unified Device Architecture (CUDA), C, C++, Java, Python, and the like; and using standard machine learning/deep learning library (or API), such as tensorflow, torch and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A method comprising:
   receiving first and second images depicting an anatomy of a subject, the first image corresponding to a previous radiotherapy treatment fraction, the second image corresponding to a current radiotherapy treatment fraction;
   applying a first sub-network of a trained neural network to the first image and the second image to generate an initial segmentation estimate representing a deformation of a first image segmentation, associated with the first image, to fit the anatomy depicted in the second image, the first sub-network trained to establish a relationship between a plurality of previous treatment fraction images and subsequently obtained treatment fraction images;
   applying a second sub-network of the trained neural network to the initial segmentation estimate and the second image to predict a refined segmentation for the second image, the second sub-network trained to establish a relationship between a plurality of initial segmentation estimates of a plurality of current fraction images and ground truth segmentations of the plurality of current fraction images; and
   configuring a radiotherapy treatment parameter based on the refined segmentation of the second image.

2. The method of claim 1, wherein the first and second sub-networks are components of a single deep convolutional neural network for contour adaptation.

3. The method of claim 1, wherein applying the first sub-network to the first image and the second image comprises:
   concatenating the first and second images along a channel dimension to generate concatenated data; and
   generating, based on a passing the concatenated data through the first sub-network, a deformation vector field (DVF) that maps pixels or voxels from the first image to the second image.

4. The method of claim 3, further comprising:
   resampling the first image with the first image segmentation based on the DVF to produce an image-segmentation pair that aligns the first image to the second image.

5. The method of claim 3, further comprising:
   deforming the first image segmentation based on the DVF.

6. The method of claim 5, wherein applying the second sub-network to the initial segmentation estimate and the second image to predict the refined segmentation for the second image comprises:
   applying the second sub-network to the deformed segmentation and the second image to generate the refined segmentation.

7. The method of claim 1, further comprising:
   converting one or more contours associated with the first image to label maps or binary segmentations to generate the first image segmentation.

8. The method of claim 1, wherein configuring the radiotherapy treatment parameter comprises converting the refined segmentation of the second image to one or more contours associated with the second image.

9. The method of claim 1, further comprising:
   determining a first modality of the first image; and
   adjusting a second image obtained using a second modality to correspond to the first modality of the first image.

10. The method of claim 1, wherein configuring the radiotherapy treatment parameter comprises at least one of recalculating dose, adjusting one or more radiotherapy treatment machine parameters, or generating a display of the second image with the refined segmentation of the second image on a graphical user interface.

11. The method of claim 1, further comprising training the first and second sub-networks simultaneously by performing training operations comprising:
  obtaining a pair of training images and corresponding ground truth segmentations representing two treatment fractions;
  applying the first sub-network to the pair of training images and the ground truth segmentation corresponding to a first training image of the pair of training images to generate a first initial estimated segmentation;
  applying the second sub-network to a second training image of the pair of training images and the first initial estimated segmentation to generate a refined segmentation;
  computing a set of cost functions the set of cost functions including a term which measures a discrepancy between the refined segmentation and the ground truth segmentation; and
  adjusting one or more parameters of at least one of the first sub-network or the second sub-network based on the computed cost function.

12. The method of claim 11, wherein computing the set of cost functions further comprises computing a cost function that includes a difference between a deformation of a given one of the plurality of previous treatment fraction images and a given one of the subsequently obtained treatment fraction images.

13. The method of claim 11, wherein computing the set of cost functions further comprises computing an additional cost function that includes a difference between a deformation of a segmentation associated with a given one of the plurality of previous treatment fraction images and a ground truth segmentation of the given one of the subsequently obtained treatment fraction images.

14. The method of claim 11, wherein computing the set of cost functions further comprises computing an additional cost function that includes a measure of smoothness of a generated deformation field.

15. The method of claim 1, further comprising training the first and second sub-networks in sequence by first adjusting one or more parameters of the first sub-network to minimize a first set of cost functions and then adjusting one or more parameters of the second sub-network to minimize a second set of cost functions.

16. The method of claim 15, further comprising training the first sub-network by performing training operations comprising:
  obtaining a pair of training images and corresponding ground truth segmentations representing two treatment fractions;
  applying the first sub-network to the pair of training images and the ground truth segmentation corresponding to a first training image in the pair of training images to generate at least one of a deformation of the first training image or a deformation of a segmentation of the first training image;
  computing a first set of cost functions, the set of cost functions including a term which measures a discrepancy between the initial segmentation and the ground truth segmentation corresponding to the second training image; and
  adjusting one or more parameters of the first sub-network based on the computed first set of cost functions.

17. The method of claim 16, further comprising training the second sub-network by performing training operations comprising:
  applying the second sub-network to the second training image and the first initial estimated segmentation to generate a refined segmentation;
  computing a second set of cost functions, the set of cost functions including a term which measures a discrepancy between the refined segmentation and the ground truth segmentation corresponding to the second training image; and
  adjusting one or more parameters of at least one of the first sub-network or the second sub-network based on the computed first or second sets of cost functions.

18. A computing apparatus comprising:
  at least one processor; and
  a memory storing instructions that, when executed by the at least one processor, configure the computing apparatus to perform operations comprising:
    receiving first and second images depicting an anatomy of a subject, the first image corresponding to a previous radiotherapy treatment fraction, the second image corresponding to a current radiotherapy treatment fraction;
    applying a first sub-network of a trained neural network to the first image and the second image to generate an initial segmentation estimate representing a deformation of a first image segmentation, associated with the first image, to fit the anatomy depicted in the second image, the first sub-network trained to establish a relationship between a plurality of previous treatment fraction images and subsequently obtained treatment fraction images;
    applying a second sub-network of the trained neural network to the initial segmentation estimate and the second image to predict a refined segmentation for the second image, the second sub-network trained to establish a relationship between a plurality of initial segmentation estimates of a plurality of current fraction images and ground truth segmentations of the plurality of current fraction images; and
    configuring a radiotherapy treatment parameter based on the refined segmentation of the second image.

19. The computing apparatus of claim 18, wherein the first and second sub-networks are components of a single deep convolutional neural network for contour adaptation.

20. The computing apparatus of claim 18, wherein applying the first sub-network to the first image and the second image comprises:
  concatenating the first and second images along a channel dimension to generate concatenated data; and
  generating, based on a passing the concatenated data through the first sub-network, a deformation vector field (DVF) that maps pixels or voxels from the first image to the second image.

21. The computing apparatus of claim 20, wherein the instructions further configure the apparatus to:
  resample the first image with the first image segmentation based on the DVF to produce an image-segmentation pair that aligns the first image to the second image.

22. The computing apparatus of claim 20, wherein the instructions further configure the apparatus to:
  deform the first image segmentation based on the DVF.

23. The computing apparatus of claim 22, wherein applying the second sub-network to the initial segmentation estimate and the second image to predict the refined segmentation for the second image comprises:
applying the second sub-network to the deformed segmentation and the second image to generate the refined segmentation.

24. The computing apparatus of claim 18, wherein the instructions further configure the apparatus to:
convert one or more contours associated with the first image to label maps or binary segmentations to generate the first image segmentation.

25. The computing apparatus of claim 18, wherein configuring the radiotherapy treatment parameter comprises converting the refined segmentation of the second image to one or more contours associated with the second image.

26. The computing apparatus of claim 18, wherein the instructions further configure the apparatus to:
determine a first modality of the first image; and
adjust a second image obtained using a second modality to correspond to the first modality of the first image.

27. The computing apparatus of claim 18, wherein configuring the radiotherapy treatment parameter comprises at least one of recalculating dose, adjusting one or more radiotherapy treatment machine parameters, or generating a display of the second image with the refined segmentation of the second image on a graphical user interface.

28. The computing apparatus of claim 18, wherein the instructions further configure the apparatus to train the first and second sub-networks simultaneously by performing training operations comprising:
obtaining a pair of training images and corresponding ground truth segmentations representing two treatment fractions;
applying the first sub-network to the pair of training images and the ground truth segmentation corresponding to a first training image of the pair of training images to generate a first initial estimated segmentation;
applying the second sub-network to a second training image of the pair of training images and the first initial estimated segmentation to generate a refined segmentation;
computing a set of cost functions, the set of cost functions including a term which measures a discrepancy between the refined segmentation and the ground truth segmentation; and
adjusting one or more parameters of at least one of the first sub-network or the second sub-network based on the computed cost function.

29. The computing apparatus of claim 28, wherein computing the set of cost functions further comprises computing an additional cost function that includes a difference between a deformation of a given one of the plurality of previous treatment fraction images and a given one of the subsequently obtained treatment fraction images.

30. The computing apparatus of claim 28, wherein computing the set of cost functions further comprises computing an additional cost function that includes a difference between a deformation of a segmentation associated with a given one of the plurality of previous treatment fraction images and a ground truth segmentation of the given one of the subsequently obtained treatment fraction images.

31. The computing apparatus of claim 28, wherein computing the set of cost functions further comprises computing an additional cost function that includes a measure of smoothness of a generated deformation field.

32. The computing apparatus of claim 18, wherein the instructions further configure the apparatus to train the first and second sub-networks in sequence by first adjusting one or more parameters of the first sub-network to minimize a first set of cost functions and then adjusting one or more parameters of the second sub-network to minimize a second set of cost functions.

33. A non-transitory computer-readable storage medium, the computer-readable storage medium including instructions that when executed by a computer, cause the computer to perform operations comprising:
receiving first and second images depicting an anatomy of a subject, the first image corresponding to a previous radiotherapy treatment fraction, the second image corresponding to a current radiotherapy treatment fraction;
applying a first sub-network of a trained neural network to the first image and the second image to generate an initial segmentation estimate representing a deformation of a first image segmentation, associated with the first image, to fit the anatomy depicted in the second image, the first sub-network trained to establish a relationship between a plurality of previous treatment fraction images and subsequently obtained treatment fraction images;
applying a second sub-network of the trained neural network to the initial segmentation estimate and the second image to predict a refined segmentation for the second image, the second sub-network trained to establish a relationship between a plurality of initial segmentation estimates of a plurality of current fraction images and ground truth segmentations of the plurality of current fraction images; and
configuring a radiotherapy treatment parameter based on the refined segmentation of the second image.

* * * * *